(12) United States Patent
Seme et al.

(10) Patent No.: US 8,357,183 B2
(45) Date of Patent: Jan. 22, 2013

(54) SEMI-CONSTRAINED ANCHORING SYSTEM

(75) Inventors: Steven J. Seme, Savage, MN (US); Thomas J. Gisel, Chaska, MN (US)

(73) Assignee: Kspine, Inc., Minnetonka, MN (US)

( * ) Notice: Subject to any disclaimer, the term of this patent is extended or adjusted under 35 U.S.C. 154(b) by 689 days.

(21) Appl. No.: 12/411,562

(22) Filed: Mar. 26, 2009

(65) Prior Publication Data

US 2010/0249837 A1    Sep. 30, 2010

(51) Int. Cl.
   *A61B 17/70*    (2006.01)
(52) U.S. Cl. .................. 606/257; 606/258; 606/260
(58) Field of Classification Search .......... 606/246–279, 606/86 R
   See application file for complete search history.

(56) References Cited

U.S. PATENT DOCUMENTS

| | | |
|---|---|---|
| 2,774,350 A | 12/1956 | Cleveland, Jr. |
| 3,352,226 A | 11/1967 | Nelsen |
| 3,648,691 A | 3/1972 | Lumb et al. |
| 3,693,616 A | 9/1972 | Roaf et al. |
| 3,865,105 A | 2/1975 | Lode |
| 4,024,588 A | 5/1977 | Janssen et al. |
| 4,078,559 A | 3/1978 | Nissinen |
| 4,257,409 A | 3/1981 | Bacal et al. |
| 4,269,178 A | 5/1981 | Keene |
| 4,274,401 A | 6/1981 | Miskew |
| 4,355,645 A | 10/1982 | Mitani et al. |
| 4,361,141 A | 11/1982 | Tanner |
| 4,369,769 A | 1/1983 | Edwards |
| 4,404,967 A | 9/1983 | Bacal et al. |
| 4,411,259 A | 10/1983 | Drummond |
| 4,411,545 A | 10/1983 | Roberge |
| 4,448,191 A | 5/1984 | Rodnyansky et al. |
| 4,505,268 A | 3/1985 | Sgandurra |
| 4,554,914 A | 11/1985 | Kapp et al. |
| 4,573,454 A | 3/1986 | Hoffman |
| 4,604,995 A | 8/1986 | Stephens et al. |
| 4,611,581 A | 9/1986 | Steffee |
| 4,611,582 A | 9/1986 | Duff |
| 4,648,388 A | 3/1987 | Steffee |
| 4,653,481 A | 3/1987 | Howland et al. |
| 4,658,809 A | 4/1987 | Ulrich et al. |
| 4,697,582 A | 10/1987 | William |
| 4,738,251 A | 4/1988 | Plaza |
| 4,773,402 A | 9/1988 | Asher et al. |
| 4,805,602 A | 2/1989 | Puno et al. |
| 4,815,453 A | 3/1989 | Cotrel |
| 4,827,918 A | 5/1989 | Olerud |

(Continued)

FOREIGN PATENT DOCUMENTS

DE    2644735 A1    4/1977

(Continued)

OTHER PUBLICATIONS

International Search Report and Written Opinion issued in PCT/US2010/028684, mailed Sep. 28, 2010, 19 pages.

(Continued)

*Primary Examiner* — Alvin Stewart
*Assistant Examiner* — Tara Carter
(74) *Attorney, Agent, or Firm* — Faegre Baker Daniels LLP

(57) ABSTRACT

Systems, devices, and associated methods for correcting spinal column deformities that help minimize a number of attachment anchors utilized for correction, facilitate use of straight or contoured rods, and/or help promote a more natural, physiologic motion of the spinal column.

21 Claims, 11 Drawing Sheets

U.S. PATENT DOCUMENTS

| | | | |
|---|---|---|---|
| 4,854,311 A | 8/1989 | Steffee |
| 4,931,055 A | 6/1990 | Bumpus et al. |
| 4,936,848 A | 6/1990 | Bagby |
| 5,000,166 A | 3/1991 | Karpf |
| 5,005,562 A | 4/1991 | Cotrel |
| 5,011,484 A | 4/1991 | Breard |
| 5,030,220 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,127,912 A | 7/1992 | Ray et al. |
| 5,129,900 A | 7/1992 | Asher et al. |
| 5,133,716 A | 7/1992 | Plaza |
| 5,147,363 A | 9/1992 | Härle |
| 5,176,679 A | 1/1993 | Lin |
| 5,176,680 A | 1/1993 | Vignaud et al. |
| 5,181,917 A | 1/1993 | Rogozinski |
| 5,190,543 A | 3/1993 | Schläpfer |
| 5,196,014 A | 3/1993 | Lin |
| 5,207,678 A | 5/1993 | Harms et al. |
| 5,209,752 A | 5/1993 | Ashman et al. |
| 5,219,349 A | 6/1993 | Krag et al. |
| 5,242,443 A | 9/1993 | Kambin |
| 5,254,118 A | 10/1993 | Mirkovic |
| 5,257,994 A | 11/1993 | Lin |
| 5,259,398 A | 11/1993 | Vrespa |
| 5,282,862 A | 2/1994 | Baker et al. |
| 5,306,275 A | 4/1994 | Bryan |
| 5,312,404 A | 5/1994 | Asher et al. |
| 5,312,410 A | 5/1994 | Miller et al. |
| 5,312,420 A | 5/1994 | Toso et al. |
| 5,330,474 A | 7/1994 | Lin |
| 5,352,226 A | 10/1994 | Lin |
| 5,366,455 A | 11/1994 | Dove et al. |
| 5,368,594 A | 11/1994 | Martin et al. |
| 5,380,323 A | 1/1995 | Howland |
| 5,380,325 A | 1/1995 | Lahille et al. |
| 5,382,248 A | 1/1995 | Jacobson et al. |
| 5,387,212 A | 2/1995 | Yuan et al. |
| 5,387,213 A | 2/1995 | Breard et al. |
| 5,391,168 A | 2/1995 | Sanders et al. |
| 5,397,363 A | 3/1995 | Gelbard |
| 5,413,576 A | 5/1995 | Rivard |
| 5,436,542 A | 7/1995 | Petelin et al. |
| 5,437,669 A | 8/1995 | Yuan et al. |
| 5,437,671 A | 8/1995 | Lozier et al. |
| 5,456,722 A | 10/1995 | McLeod et al. |
| 5,470,333 A | 11/1995 | Ray |
| 5,480,440 A | 1/1996 | Kambin |
| 5,486,174 A | 1/1996 | Fournet-Fayard et al. |
| 5,487,744 A | 1/1996 | Howland |
| 5,490,851 A | 2/1996 | Nenov et al. |
| 5,496,318 A | 3/1996 | Howland et al. |
| 5,498,262 A | 3/1996 | Bryan |
| 5,501,684 A | 3/1996 | Schlapfer et al. |
| 5,520,688 A | 5/1996 | Lin |
| 5,540,689 A | 7/1996 | Sanders et al. |
| 5,544,993 A | 8/1996 | Härle |
| 5,549,679 A | 8/1996 | Kuslich |
| 5,562,660 A | 10/1996 | Grob |
| 5,562,662 A | 10/1996 | Brumfield et al. |
| 5,569,246 A | 10/1996 | Ojima et al. |
| 5,571,191 A | 11/1996 | Fitz |
| 5,575,791 A | 11/1996 | Lin |
| 5,584,626 A | 12/1996 | Assmundson |
| 5,586,983 A | 12/1996 | Sanders et al. |
| 5,591,165 A | 1/1997 | Jackson |
| 5,611,800 A | 3/1997 | Davis et al. |
| 5,643,259 A | 7/1997 | Sasso et al. |
| 5,645,599 A | 7/1997 | Samani |
| 5,649,926 A | 7/1997 | Howland |
| 5,658,284 A | 8/1997 | Sebastián et al. |
| 5,672,175 A * | 9/1997 | Martin ................. 606/86 A |
| 5,676,703 A | 10/1997 | Gelbard |
| 5,702,395 A | 12/1997 | Hopf |
| 5,702,399 A | 12/1997 | Kilpela et al. |
| 5,702,452 A | 12/1997 | Argenson et al. |
| 5,704,936 A | 1/1998 | Mazel |
| 5,713,898 A | 2/1998 | Stücker et al. |
| 5,725,582 A | 3/1998 | Bevan et al. |
| 5,728,097 A | 3/1998 | Mathews |
| 5,733,284 A | 3/1998 | Martin |
| 5,735,852 A | 4/1998 | Amrein et al. |
| 5,782,831 A | 7/1998 | Sherman et al. |
| 5,797,910 A | 8/1998 | Martin |
| 5,810,817 A | 9/1998 | Roussouly et al. |
| 5,810,819 A | 9/1998 | Errico et al. |
| 5,814,046 A | 9/1998 | Hopf |
| 5,891,145 A | 4/1999 | Morrison et al. |
| 5,902,305 A | 5/1999 | Beger et al. |
| 5,910,142 A | 6/1999 | Tatar |
| 5,928,232 A | 7/1999 | Howland et al. |
| 5,938,663 A | 8/1999 | Petreto |
| 5,947,967 A | 9/1999 | Barker |
| 5,964,769 A | 10/1999 | Wagner et al. |
| 5,976,135 A | 11/1999 | Sherman et al. |
| 5,980,521 A | 11/1999 | Montague et al. |
| 5,984,924 A | 11/1999 | Asher et al. |
| 5,989,256 A | 11/1999 | Kuslich et al. |
| 6,015,409 A | 1/2000 | Jackson |
| 6,039,738 A | 3/2000 | Sanders et al. |
| 6,053,921 A | 4/2000 | Wagner et al. |
| 6,077,268 A | 6/2000 | Farris et al. |
| 6,080,156 A | 6/2000 | Asher et al. |
| 6,086,590 A | 7/2000 | Margulies et al. |
| 6,123,706 A | 9/2000 | Lange |
| 6,132,431 A | 10/2000 | Nilsson et al. |
| 6,132,464 A | 10/2000 | Martin |
| 6,136,000 A | 10/2000 | Louis |
| 6,176,861 B1 | 1/2001 | Bernstein et al. |
| 6,231,575 B1 | 5/2001 | Krag |
| 6,248,106 B1 | 6/2001 | Ferree |
| 6,251,111 B1 | 6/2001 | Barker et al. |
| 6,261,288 B1 | 7/2001 | Jackson |
| 6,277,120 B1 | 8/2001 | Lawson |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,325,805 B1 | 12/2001 | Ogilvie et al. |
| 6,328,739 B1 | 12/2001 | Liu et al. |
| 6,358,254 B1 | 3/2002 | Anderson |
| 6,364,883 B1 | 4/2002 | Santilli |
| 6,364,885 B1 | 4/2002 | Kilpela et al. |
| 6,391,030 B1 | 5/2002 | Wagner et al. |
| 6,402,752 B2 | 6/2002 | Schaffler-Wachter et al. |
| 6,419,703 B1 | 7/2002 | Fallin et al. |
| 6,423,065 B2 | 7/2002 | Ferree |
| 6,451,019 B1 | 9/2002 | Zucherman et al. |
| 6,458,131 B1 | 10/2002 | Ray |
| 6,488,683 B2 | 12/2002 | Lieberman |
| 6,514,255 B1 | 2/2003 | Ferree |
| 6,520,962 B1 | 2/2003 | Taylor et al. |
| 6,537,276 B2 | 3/2003 | Metz-Stavenhagen |
| 6,547,789 B1 | 4/2003 | Ventre et al. |
| 6,551,320 B2 | 4/2003 | Lieberman |
| 6,554,831 B1 | 4/2003 | Rivard et al. |
| 6,562,038 B1 | 5/2003 | Morrison |
| 6,565,569 B1 | 5/2003 | Assaker et al. |
| 6,569,164 B1 | 5/2003 | Assaker et al. |
| 6,579,292 B2 | 6/2003 | Taylor |
| 6,579,319 B2 | 6/2003 | Goble et al. |
| 6,582,433 B2 | 6/2003 | Yun |
| 6,589,243 B1 | 7/2003 | Viart et al. |
| 6,610,091 B1 | 8/2003 | Reiley |
| 6,616,669 B2 | 9/2003 | Ogilvie et al. |
| 6,623,484 B2 | 9/2003 | Betz et al. |
| 6,626,906 B1 | 9/2003 | Young |
| 6,626,909 B2 | 9/2003 | Chin |
| 6,645,207 B2 | 11/2003 | Dixon et al. |
| 6,651,320 B1 | 11/2003 | Yagi et al. |
| 6,656,185 B2 | 12/2003 | Gleason et al. |
| 6,669,729 B2 | 12/2003 | Chin |
| 6,682,532 B2 | 1/2004 | Johnson et al. |
| 6,682,533 B1 | 1/2004 | Dinsdale et al. |
| 6,685,705 B1 | 2/2004 | Taylor |
| 6,689,133 B2 | 2/2004 | Morrison et al. |

| Patent/Pub No. | Date | Name |
|---|---|---|
| 6,709,435 B2 | 3/2004 | Lin |
| 6,755,828 B2 | 6/2004 | Shevtsov et al. |
| 6,773,437 B2 | 8/2004 | Ogilvie et al. |
| 6,802,844 B2 | 10/2004 | Ferree |
| 6,835,207 B2 | 12/2004 | Zacouto et al. |
| 6,840,127 B2 | 1/2005 | Moran |
| 6,860,884 B2 | 3/2005 | Shirado et al. |
| 6,946,000 B2 | 9/2005 | Senegas et al. |
| 6,966,910 B2 | 11/2005 | Ritland |
| 6,966,930 B2 | 11/2005 | Arnin et al. |
| 6,986,771 B2 | 1/2006 | Paul et al. |
| 7,018,379 B2 | 3/2006 | Drewry et al. |
| 7,029,475 B2 | 4/2006 | Panjabi |
| 7,048,736 B2 | 5/2006 | Robinson et al. |
| 7,074,237 B2 | 7/2006 | Goble et al. |
| 7,083,621 B2 | 8/2006 | Shaolian et al. |
| 7,087,056 B2 | 8/2006 | Vaughan |
| 7,104,992 B2 | 9/2006 | Bailey |
| RE39,325 E | 10/2006 | Bryan |
| 7,128,743 B2 | 10/2006 | Metz-Stavenhagen |
| 7,160,312 B2 | 1/2007 | Saadat |
| 7,220,262 B1 | 5/2007 | Hynes |
| 7,270,665 B2 | 9/2007 | Morrison et al. |
| 7,294,129 B2 | 11/2007 | Hawkins et al. |
| 7,316,684 B1 | 1/2008 | Baccelli et al. |
| 7,335,203 B2 | 2/2008 | Winslow et al. |
| 7,338,490 B2 | 3/2008 | Ogilvie et al. |
| 7,344,539 B2 | 3/2008 | Serhan et al. |
| 7,361,196 B2 | 4/2008 | Fallin et al. |
| 7,367,978 B2 | 5/2008 | Drewry et al. |
| 7,481,828 B2 | 1/2009 | Mazda et al. |
| 7,524,324 B2 | 4/2009 | Winslow et al. |
| 7,611,526 B2 | 11/2009 | Carl et al. |
| 7,658,753 B2 | 2/2010 | Carl et al. |
| 7,819,902 B2 | 10/2010 | Abdelgany et al. |
| 8,016,860 B2 | 9/2011 | Carl et al. |
| 8,043,345 B2 | 10/2011 | Carl et al. |
| 8,097,022 B2 | 1/2012 | Marik |
| 8,114,158 B2 | 2/2012 | Carl et al. |
| 8,162,979 B2 | 4/2012 | Sachs et al. |
| 2001/0037111 A1 | 11/2001 | Dixon et al. |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2003/0040746 A1 | 2/2003 | Mitchell et al. |
| 2003/0093117 A1 | 5/2003 | Saadat |
| 2003/0109881 A1 | 6/2003 | Shirado et al. |
| 2003/0153915 A1 | 8/2003 | Nekozuka et al. |
| 2003/0220643 A1 | 11/2003 | Ferree |
| 2004/0097931 A1 | 5/2004 | Mitchell |
| 2004/0106921 A1 | 6/2004 | Cheung et al. |
| 2004/0149065 A1 | 8/2004 | Moran |
| 2004/0167520 A1 | 8/2004 | Zucherman et al. |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0033295 A1 | 2/2005 | Wisnewski |
| 2005/0043797 A1 | 2/2005 | Lee |
| 2005/0055096 A1 | 3/2005 | Serhan et al. |
| 2005/0080420 A1 | 4/2005 | Farris et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson-MacDonald et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2006/0009767 A1 | 1/2006 | Kiester |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0058792 A1 | 3/2006 | Hynes |
| 2006/0064091 A1 | 3/2006 | Ludwig et al. |
| 2006/0084976 A1 | 4/2006 | Borgstrom et al. |
| 2006/0084996 A1 | 4/2006 | Metz-Stavenhagen |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0217712 A1 | 9/2006 | Mueller et al. |
| 2006/0217715 A1 | 9/2006 | Serhan et al. |
| 2006/0241594 A1 | 10/2006 | McCarthy et al. |
| 2006/0247627 A1 | 11/2006 | Farris |
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0293663 A1 | 12/2006 | Walkenhorst et al. |
| 2007/0005062 A1 | 1/2007 | Lange et al. |
| 2007/0055373 A1 | 3/2007 | Hudgins et al. |
| 2007/0073293 A1 | 3/2007 | Martz et al. |
| 2007/0083200 A1 | 4/2007 | Gittings et al. |
| 2007/0093814 A1 | 4/2007 | Callahan, II et al. |
| 2007/0161987 A1 | 7/2007 | Capote et al. |
| 2007/0161994 A1 | 7/2007 | Lowery et al. |
| 2007/0162002 A1 | 7/2007 | Tornier |
| 2007/0167947 A1 | 7/2007 | Gittings |
| 2007/0168035 A1 | 7/2007 | Koske |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1 | 10/2007 | Falahee |
| 2007/0238335 A1 | 10/2007 | Veldman et al. |
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0288011 A1 | 12/2007 | Logan |
| 2007/0288024 A1 | 12/2007 | Gollogly |
| 2008/0015577 A1 | 1/2008 | Loeb |
| 2008/0021466 A1 | 1/2008 | Shadduck et al. |
| 2008/0021469 A1 | 1/2008 | Holt |
| 2008/0065069 A1 | 3/2008 | Betz et al. |
| 2008/0077143 A1 | 3/2008 | Shluzas |
| 2008/0097441 A1 | 4/2008 | Hayes et al. |
| 2008/0140202 A1 | 6/2008 | Allard et al. |
| 2008/0177326 A1 | 7/2008 | Thompson |
| 2008/0183209 A1 | 7/2008 | Robinson et al. |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0228227 A1 | 9/2008 | Brown et al. |
| 2008/0234737 A1 | 9/2008 | Boschert |
| 2008/0234739 A1 | 9/2008 | Hudgins et al. |
| 2008/0262546 A1 | 10/2008 | Calvosa et al. |
| 2008/0306535 A1 | 12/2008 | Winslow et al. |
| 2008/0306536 A1 | 12/2008 | Frigg et al. |
| 2009/0012565 A1 | 1/2009 | Sachs et al. |
| 2009/0018583 A1 | 1/2009 | Song et al. |
| 2009/0024166 A1 | 1/2009 | Carl et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0062915 A1 | 3/2009 | Kohm et al. |
| 2009/0069849 A1 | 3/2009 | Oh et al. |
| 2009/0093820 A1 | 4/2009 | Trieu et al. |
| 2009/0099607 A1 | 4/2009 | Fallin et al. |
| 2009/0112207 A1 | 4/2009 | Walker et al. |

| | | | |
|---|---|---|---|
| 2009/0112262 | A1 | 4/2009 | Pool et al. |
| 2009/0112263 | A1 | 4/2009 | Pool et al. |
| 2009/0125062 | A1 | 5/2009 | Arnin |
| 2009/0194206 | A1 | 8/2009 | Jeon et al. |
| 2009/0204156 | A1 | 8/2009 | McClintock et al. |
| 2009/0259256 | A1 | 10/2009 | Miller |
| 2009/0281575 | A1 | 11/2009 | Carls et al. |
| 2010/0100130 | A1 | 4/2010 | Carl et al. |
| 2010/0100133 | A1 | 4/2010 | Carl et al. |
| 2010/0106192 | A1 | 4/2010 | Barry |
| 2010/0137913 | A1 | 6/2010 | Khatchadourian et al. |
| 2010/0249836 | A1 | 9/2010 | Seme |
| 2010/0256684 | A1 | 10/2010 | Seme et al. |
| 2010/0286730 | A1 | 11/2010 | Gordon |
| 2011/0054536 | A1 | 3/2011 | Elsebaie et al. |
| 2011/0066188 | A1 | 3/2011 | Seme et al. |
| 2012/0109197 | A1 | 5/2012 | Carl et al. |

FOREIGN PATENT DOCUMENTS

| | | |
|---|---|---|
| DE | 2845647 A1 | 5/1980 |
| EP | 0260044 A1 | 3/1988 |
| EP | 0322334 A1 | 6/1989 |
| EP | 0418387 A1 | 3/1991 |
| EP | 1281361 A1 | 2/2003 |
| FR | 2697744 A1 | 5/1994 |
| FR | 2736535 A1 | 1/1997 |
| FR | 2781359 A1 | 1/2000 |
| FR | 2801492 A1 | 6/2001 |
| FR | 2872021 A1 | 12/2005 |
| GB | 780652 | 12/1957 |
| SU | 888968 | 12/1981 |
| WO | WO 92/13496 | 8/1992 |
| WO | WO2004017705 A2 | 3/2004 |
| WO | WO 2006/010844 A1 | 2/2006 |
| WO | WO2006017641 A2 | 2/2006 |
| WO | WO 2006/136937 A2 | 12/2006 |
| WO | WO 2007/051924 A1 | 5/2007 |
| WO | 2008086467 A2 | 7/2008 |
| WO | WO2008154313 A1 | 12/2008 |
| WO | WO 2010/053662 | 5/2010 |
| WO | WO 2010/056650 | 5/2010 |
| WO | 2010111500 A1 | 9/2010 |

OTHER PUBLICATIONS

International Search Report and Written Opinion issued in PCT/US2010/036375, mailed Sep. 10, 2010, 16 pages.
Steven J. Seme, Alignment System with Longitudinal Support Features, U.S. Appl. No. 12/411,558, filed Mar. 26, 2009.
International Search Report and Written Opinion issued in PCT/US2010/047117, mailed Dec. 2, 2010.
International Search Report and Written Opinion issued in PCT/US2011/049693, mailed Nov. 15, 2011, 16 pages.
International Search Report and Written Opinion of the International Searching Authority, International Application No. PCT/US2008/065979, mailed Oct. 2, 2008; Published Application, WO2008/154313, International Application No. PCT/US2008/065979, published Dec. 18, 2008.
International Preliminary Report on Patentability and Written Opinion of the International Searching Authority, International Application No. PCT/US2005/027692; mailed May 19, 2008; Published Application, WO2006/017641, International Application No. PCTUS2005/027692, published Feb. 16, 2006.
Invitation to Pay Additional Fees and Partial Search Report issued in PCT/US2010/028684, mailed Jun. 30, 2010.
International Search Report and Written Opinion issued in PCT/US2009/063833, mailed Mar. 15, 2010, 14 pages.
International Application No. PCT/US2008/065979, filed Jun. 5, 2008, entitled Medical Device and Method to Correct Deformity.
International Application No. PCT/US2009/063833, filed Nov. 10, 2009, entitled Growth Directed Vertebral Fixation System With Distractible Connector(s) and Apical Control.
U.S. Appl. No. 12/485,796, filed Jun. 16, 2009 entitled Deformity Alignment System With Reactive Force Balancing.
U.S. Appl. No. 12/560,199, filed Sep. 15, 2009, entitled Growth Modulation System.
Berry, James L. et al., *A Morphometric Study of Human Lumbar and Selected Thoracic Vertebrae*, 12 SPINE 362 (1987).
Fujita, Masaru et al., *A Biomechanical Analysis of Sublaminar and Subtransverse Process Fixation Using Metal Wires and Polyethylene Cables*, 31 SPINE 2202 (2006).
Girardi, Federico P. et al., *Safety of Sublaminar Wires With Isola Instrumentation for the Treatment of Idiopathic Scoliosis*, 25 SPINE 691 (2000).
Liljenqvist, Ulf R. et al., *Analysis of Vertebral Morphology in Idiopathic Scoliosis with Use of Magnetic Resonance Imaging and Multiplanar Reconstruction*, 84 J Bone Joint Surg Am. 359 (2002).
Molnar, Szabolcs et al., Ex Vivo *and* in Vitro *Determination of the Axial Rotational Axis of the Human Thoracic Spine*, 31 SPINE E984 (2006).
Rajasekaran S. et al., *Eighteen-Level Analysis of Vertebral Rotation Following Harrington-Luque Instrumentation in Idiopathic Scoliosis*, 76 J Bone Joint Surg Am. 104 (1994).
Wegner, Dennis R. et al., *Biomechanics of Scoliosis Correction by Segmental Spinal Instrumentation*, 7 SPINE 260 (1982).
White III, Augustus A. et al., Biomechancis of the Spine 28-29, Tbl. 1-5 (2d ed. 1990).

* cited by examiner

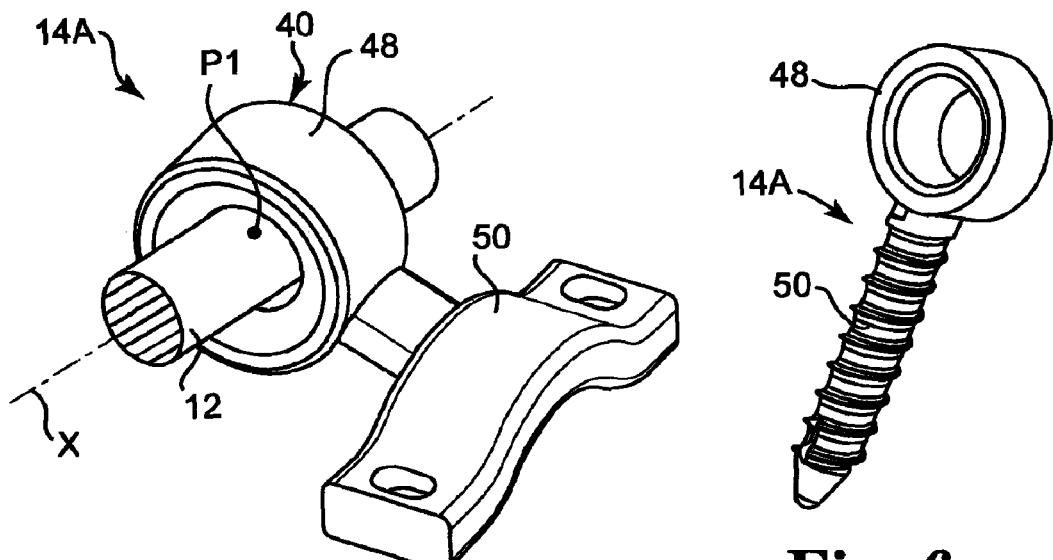
Fig. 5a
Fig. 6
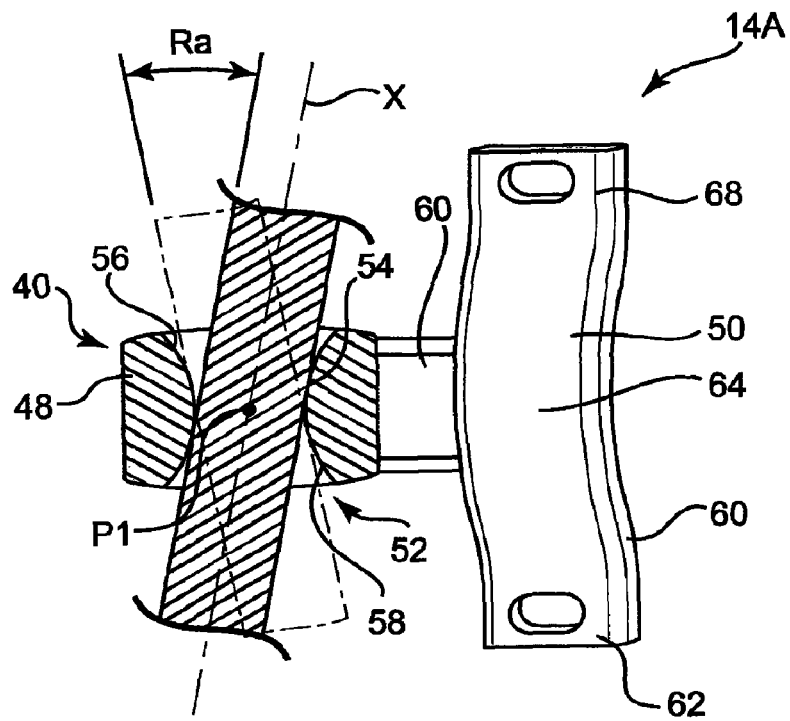
Fig. 5b

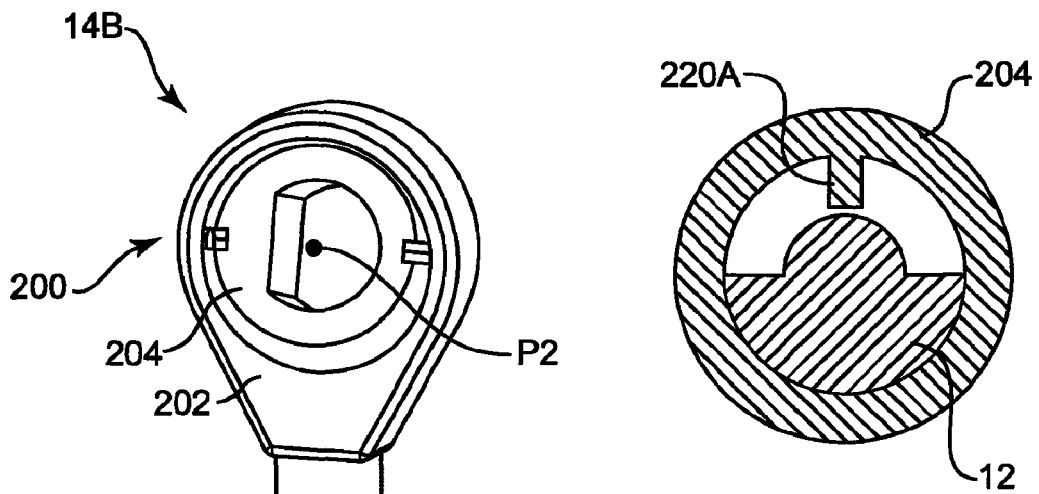
Fig. 9
Fig. 12
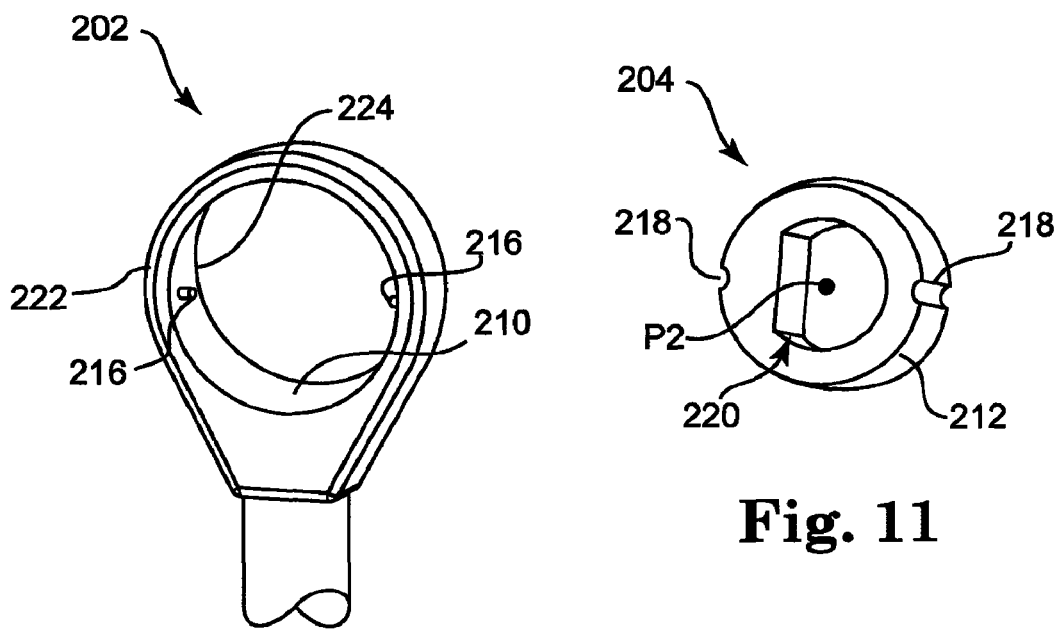
Fig. 10
Fig. 11

SEMI-CONSTRAINED ANCHORING SYSTEM

BACKGROUND

Many systems have been utilized to treat spinal deformities such as scoliosis, spondylolisthesis, and a variety of others. Primary surgical methods for correcting a spinal deformity utilize instrumentation to correct the deformity as much as possible, as well as implantable hardware systems to rigidly stabilize and maintain the correction. Presently, most of these implantable hardware systems rigidly fix the spinal column or allow limited growth and/or other movement of the spinal column, to help facilitate fusion after the column has been moved to a corrected position.

SUMMARY

Some embodiments relate to systems, devices, and associated methods for correcting spinal column deformities that help minimize a number of attachment anchors utilized for correction, facilitate use of straight or contoured rods, and/or help promote a more natural, physiologic motion of the spinal column.

Some embodiments relate to a system for correcting a spinal deformity between a first vertebra and a second vertebra of a person's spine, where the system includes a substantially rigid rod adapted to extend across the spinal deformity. The system also includes a first rod anchor adapted to be fixed to the first vertebra and to receive a first end of the rod such that the rod is allowed to translate axially relative to the first rod anchor, as well as a second rod anchor adapted to be fixed to the second vertebra and to receive a second end of the rod. A first force directing member is coupled between the rod and the spinal deformity, where the first and second rod anchors are adapted to resist lateral translation of the rod relative to the spine and to allow a longitudinal axis of the rod to change in at least a pitch and a yaw.

Some embodiments relate to exerting a distraction and/or compressive force on a spine by securing first and second rod anchors on a first side of the spine. First and second portions of a rod are received in the first and second rod anchors, respectively, such that the first and second portions are substantially constrained against lateral translation. The first and second portions are able to change in pitch and yaw at the first and second rod anchors, respectively, in response to movement of the spine. First and second stops are located adjacent the first rod anchor and the second rod anchor, respectively. The first side of the spine is distracted and/or compressed by imposing a force on the rod with the first and second stops.

This summary is not meant to be limiting in nature. While multiple embodiments are disclosed herein, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 5a, 5b, and 6 show features of an anchor of the system of FIG. 1, according to some embodiments.

FIGS. 9-11 show still another anchor of the system of FIG. 1, according to some embodiments.

FIG. 12 shows alternate complementary shapes for limiting roll between pre-selected angular limits, according to some embodiments.

Figure 1:
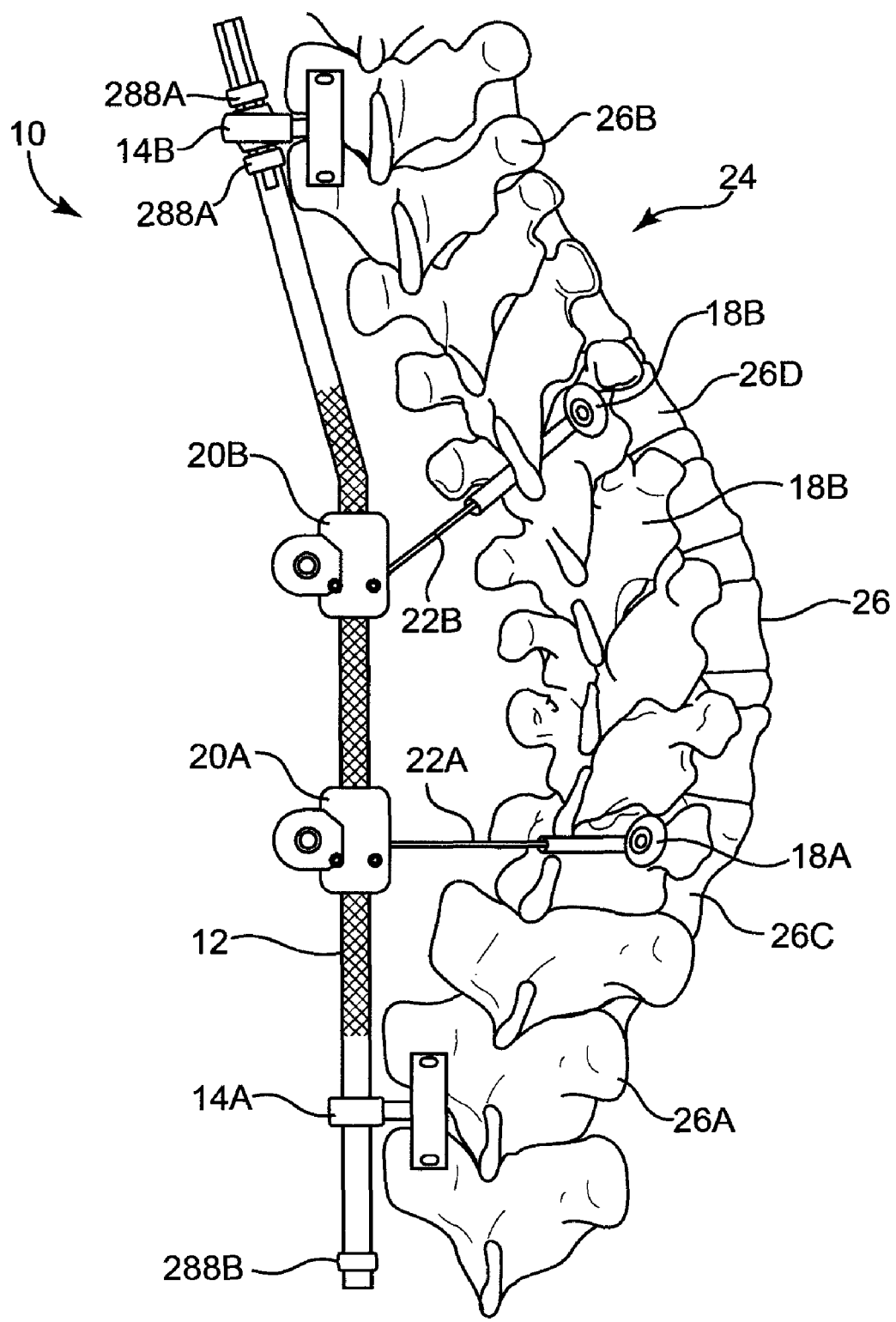
FIG. 1 shows an exemplary system for correcting a spinal deformity, according to some embodiments.

Various embodiments have been shown by way of example in the drawings and are described in detail below. As stated above, the intention, however, is not to limit the invention by providing such examples.

DETAILED DESCRIPTION

Some embodiments relate to a system for correcting spinal deformities, as well as associated methods and devices. In general terms, the system provides for lateral translational corrective force(s) and/or derotational corrective force(s) on a spinal column. Some features of the system include highly adaptive hardware for connecting the system to the spinal column, where the hardware facilitates a more natural range of motion within pre-selected limits and application of such lateral translational and/or derotational corrective force(s).

Various planes and associated directions are referenced in the following description, including a sagittal plane defined by two axes, one drawn between a head (superior) and tail (inferior) of the body and one drawn between a back (posterior) and front (anterior) of the body; a coronal plane defined by two axes, one drawn between a center (medial) to side (lateral) of the body and one drawn between a head (superior) and tail (inferior) of the body; and a transverse plane defined by two axes, one drawn between a back and front of the body and one drawing between a center and side of the body. The terms pitch, roll, and yaw are also used, where roll generally refers to angulation, or rotation, in a first plane through which a longitudinal axis of a body orthogonally passes (e.g., rotation about a longitudinal axis corresponding to the spinal column), pitch refers to angulation, or rotation, in a second plane orthogonal to the first plane, and yaw refers to angulation, or rotation, in a third plane orthogonal to the first and second planes. In some embodiments, pitch is angulation in the sagittal plane, yaw is angulation in the coronal plane, and roll is angulation in the transverse plane.

In various embodiments, changes in pitch, yaw, and/or roll occur concurrently or separately as desired. Moreover, as used herein, "lateral translation" is not limited to translation in the medial-lateral direction unless specified as such.

FIG. 1 is a perspective view of a system 10 for correcting a spinal deformity, according to some embodiments. The system 10 includes a rod 12, a plurality of rod anchors 14, including a first rod anchor 14A and a second rod anchor 14B, a plurality of vertebral anchors 18 including a first vertebral anchor 18A and a second vertebral anchor 18B, a plurality of adjustment mechanisms 20 including a first adjustment mechanism 20A and a second adjustment mechanism 20B, and a plurality of force directing members 22 including a first force directing member 22A and a second force directing member 22B. As shown, the system 10 is secured to a spinal column 24 formed of a plurality of vertebrae 26, including a first vertebra 26A, a second vertebra 26B, a third vertebra 26C, and a fourth vertebra 26D.

Although the system 10 is shown with two rod anchors 14, two vertebral anchors 18, two adjustment mechanisms 20, and two force directing members 22, more or fewer are implemented as appropriate. For example, in some embodiments a single vertebral anchor 18 is secured to a vertebra 26 at an apex of a spinal deformation or other location, with a corresponding force directing member 22 and adjustment mechanism 20 coupled to such vertebral anchor 18.

As shown in FIG. 1, however, the first and second vertebral anchors 18A, 18B are fixed to a portion of the spinal column 24 having an abnormal curvature (e.g., scoliosis) in need of correction. The system 10 is optionally used to incrementally bring the spinal column 24 to a more natural curvature, or a single adjustment is made to the system 10 to accomplish the desired curvature. In other embodiments, an abnormal curvature in the spinal column 24 has been adjusted to a more natural curvature using other hardware, prior to or in conjunction with securing the system 10 to the spinal column 24.

Figure 2:
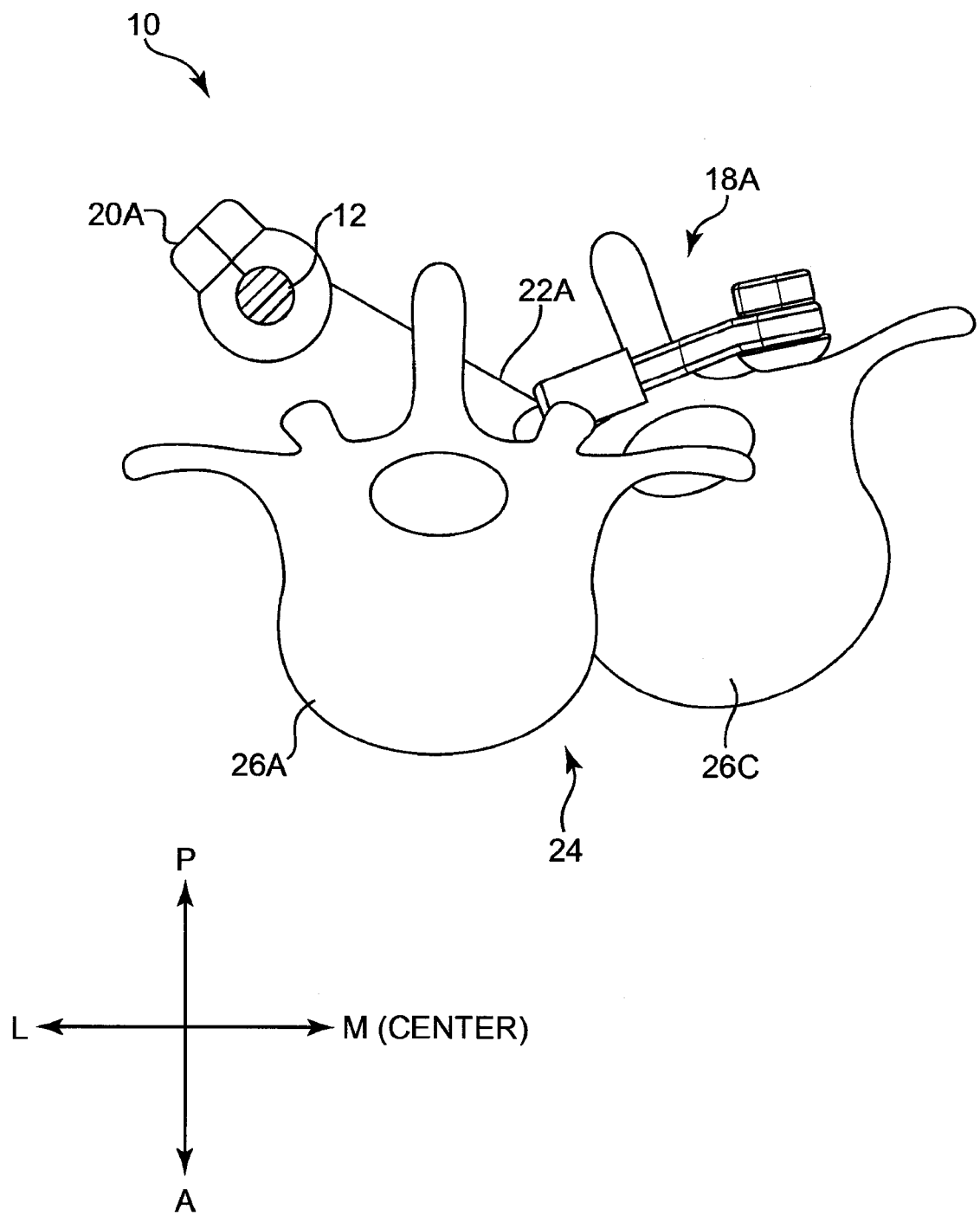
FIG. 2 is a bottom view of the system of FIG. 1 with some features not shown to facilitate understanding, according to some embodiments.

FIG. 2 shows the system 10 from a transverse plane view, with portions of the spinal column 24 and system 10 not shown for illustrative purposes. For reference, the rod 12, the first vertebral anchor 18A, the first adjustment mechanism 20A, and the first force directing member 22A are shown along with the first vertebra 26A and third vertebra 26C.

In some embodiments, the rod 12, also described as an elongate member, is secured to the spinal column 24 at a pre-selected offset from a longitudinal axis of the spinal column 24. For example, the rod 12 is optionally secured at an offset along a medial-lateral axis ML, or right-left axis, and anterior-posterior axis AP, or back-front axis. In some embodiments, the rod 12 is secured on the left side of the spinal column 24. As subsequently described, the offset is optionally selected to cause at least a relative lateral translation (e.g., central or medial movement) and derotational shift (e.g., clockwise rotation from the bottom view of FIG. 2) of selected vertebrae 26 of the spinal column 24 (relative anterior-posterior movement of selected vertebrae 26 can also be accomplished) such that the spinal column 24 exhibits a more natural position.

Figure 3:
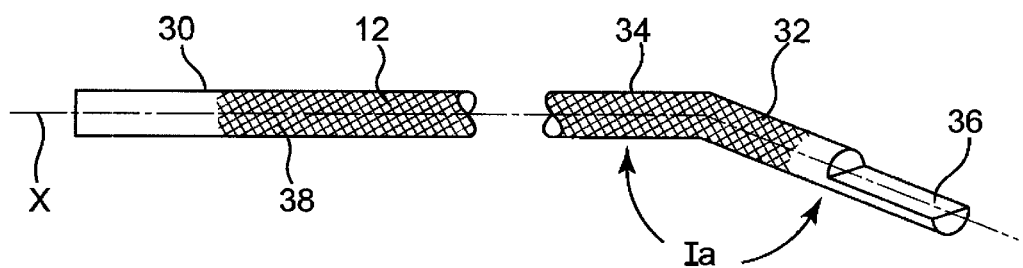
FIG. 3 shows a rod of the system of FIG. 1, according to some embodiments.

FIG. 3 shows the rod 12 having a bend according to some embodiments. In some embodiments, the rod 12 is substantially rigid, defining a substantially round cross-section with a mean diameter of about 6 mm and being formed of a suitable biocompatible material, such as titanium alloy ASTM F136. The rod 12 is adapted, or otherwise structured, to extend along the spinal column 24. In FIG. 1, the bend of the rod 12 is generally shown for illustrative purposes. In various embodiments, the rod 12 is bent in one or more of the sagittal and coronal planes. If desired, the rod 12 incorporates some flex, or springiness while substantially rigidly retaining its shape. The rod 12 is optionally formed of a variety of materials, including stainless steel or suitable polymeric materials. Moreover, as subsequently described, the cross-sectional shape of the rod 12, including various portions thereof, is not limited to circular cross-sections.

As shown in FIG. 3, in some embodiments the rod 12 is contoured or angled to at least partially mimic a curvature (e.g., sagittal plane kyphosis or lordosis or, alternatively, an existing, defective curvature, e.g., kyphosis or lordosis) of a portion of a spinal column. Although shown with a single bend, such that the rod 12 is substantially non-linear, in other embodiments the rod 12 includes substantially curved, non-linear sections, or incorporates combinations of substantially bent, straight, and/or curved sections.

The rod 12 has a longitudinal axis X, as well as a first section 30, a second section 32, and an intermediate section 34 between the first and second sections 30, 32. Where the rod 12 is substantially straight, the longitudinal axis X is substantially straight. Where the rod 12 is substantially curved or angled, the longitudinal axis X is similarly curved or angled. The sections 30, 32, 34 of the rod 12 are optionally continuously formed or are formed as separate, connected parts as desired. In some embodiments, the second section 32 and intermediate section 34 define an inner angle Ia less than 180 degrees, for example a bend angle from about 135 to about 170 degrees, although a variety of bend angles are contemplated.

Figure 4:
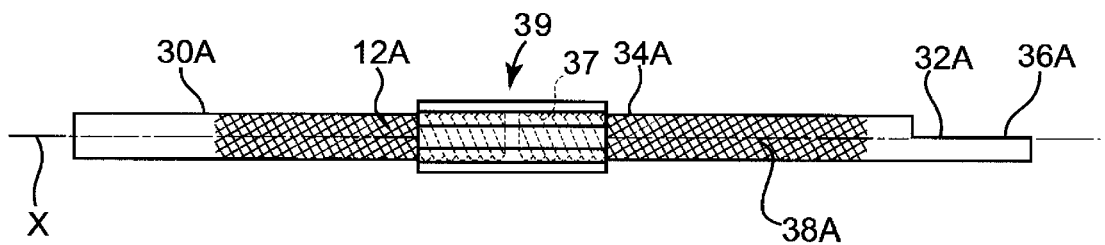
FIG. 4 shows another rod of the system of FIG. 1, according to some embodiments.

In some embodiments, at least one or both of the first and second sections 30, 32 are generally non-round or otherwise define chase features. For example, as shown in FIGS. 3 and 4, the second section 32 forms at least one flat 36, the second section 32 having a substantially D-shaped cross-section along at least a portion thereof. In turn, the first section 30 and intermediate section 34 have substantially circular cross-sections, although any of the sections 30, 32, 34 optionally have non-circular, cross-sectional shapes as desired (e.g., star-, oval-, or square-shaped cross-sections). As will be subsequently described, a cross-sectional shape of a particular section is optionally used to limit rotation of the rod 12, although cross-sectional modifications to selectively enhance bending performance and other characteristics of the rod 12 are also contemplated (e.g. I-beam, hexagonal, or other shapes).

At least some of the intermediate section 34 optionally includes a surface treatment, such as surface roughening 38 (e.g., knurling or dimpling), or other treatment (e.g., coatings, plasma treatments, or others) for enhancing friction and/or performance. In turn, portions of the first and second sections 30, 32 optionally include mirror finishes, surface coatings (e.g., PTFE), or other materials or surface treatments. Though some examples have been provided, various combinations of surface treatments for portions of each of the sections 30, 32, 34 are contemplated.

FIG. 4 shows a rod 12A according to some other embodiments. The rod 12A is substantially straight, or linear, and includes any of the features described in association with the rod 12 as appropriate. In FIG. 4 features of the rod 12A similar to those of the rod 12 are designated with the same reference number as the rod 12 followed by an "A."

In some embodiments, the rod 12A is of a two-piece design and includes a rod adjustment mechanism 39 which provides means for increasing an effective length of the rod 12A. The rod adjustment mechanism 39 is optionally a female threaded sleeve adapted to extend or contract (lengthen or shorten) a gap between pieces of the rod 12A by turning the adjustment mechanism 39 to engaging threads 37 on the sleeve. The adjustment mechanism 39 optionally has flats or other surface features for receiving a tool (e.g., an open ended wrench). One example of another female, sleeve-type adjustment mechanism generally suitable for use with some embodiments described herein is shown in U.S. Pat. No. 4,078,559, issued Mar. 14, 1978.

Additional examples of rods in accordance with some embodiments of the system 10 are set forth in U.S. application Ser. No. 11/196,952, filed on Aug. 3, 2005 and entitled DEVICE AND METHOD FOR CORRECTING A SPINAL DEFORMITY, as well as Ser. No. 12/134,058, filed on Jun. 5, 2008 and entitled MEDICAL DEVICE AND METHOD TO CORRECT DEFORMITY, the entire contents of both of which are hereby incorporated by reference.

FIGS. 5*a* and 5*b* show features of the first rod anchor 14A, according to some embodiments. As shown in FIG. 5*a*, the first rod anchor 14A is adapted, or otherwise structured, to be mounted, or fixed to one or more vertebrae, such as the first vertebra 26A (FIG. 1). The first rod anchor 14A is further adapted to receive, and includes means for receiving, the rod 12 such that the rod 12 is secured laterally, against lateral translation relative to the first rod anchor 14A. In some embodiments, the rod 12 is substantially prevented from translating in a direction substantially perpendicular to the longitudinal axis X at the first point P1. In turn, the rod 12 (shown in cut-away) is able to slide axially, or translate axially, along the longitudinal axis X, relative to the first rod anchor 14A through a first pivot point P1. The rod 12 is also able to change in pitch, yaw, and roll about the first pivot point P1.

The first rod anchor 14A is optionally formed of biocompatible metallic materials, such as titanium, stainless steel, and/or biocompatible polymeric materials, such as PEEK and/or composite materials. In some embodiments, and as shown in FIG. 5*a*, the first rod anchor 14A includes a single-piece housing 40 having receptacle portion 48 adapted, or otherwise structured, to receive the rod 12. The first rod anchor 14A further includes a mounting portion 50 adapted to secure the first rod anchor 14A to one or more vertebrae, such as the first vertebra 26A and an additional vertebra 26 above or below the first vertebra. In other embodiments, the mounting portion 50 is secured to a single vertebra, such as the first vertebra 26A (e.g., laterally across the first vertebra 26A at the pedicles, or at a single point—such as a single pedicle—on the first vertebra 26A.

As subsequently described, in some embodiments, the housing 40 is of a multi-piece design (e.g., as shown in FIGS. 7-11).

In some embodiments, the mounting portion 50, also described as a plate, is adapted to be secured at two or more points, for example spanning between two vertebrae (e.g., the L3-L4 vertebrae) or spanning across a portion of a single vertebra (e.g., pedicle-to-pedicle on a single vertebra).

FIG. 5*b* shows the receptacle portion 48 in cross-section. According to various embodiments, the receptacle portion 48 is generally ring-shaped and forms a passage 52 having a revolute, convex surface 54 having an upper curve 56 and a lower curve 58. The receptacle portion 48 is adapted to allow the rod 12 to pass through the passage 52 at the first pivot point P1, where the passage 52 defines a minimum effective diameter (e.g., providing appropriate clearance between the rod 12 and receptacle portion 48) that allows the rod 12 to slide through passage 52. The passage 52 also allows the rod 12 to rotate and angulate about the longitudinal axis X at the first pivot point P1 while minimizing lateral translation or inhibiting substantial lateral translation. In at least this manner, the rod 12 is able to rotate and angulate about the longitudinal axis X at the first pivot point while lateral translation of the rod 12 with respect to the receptacle portion 28 is substantially limited in all planes. In alternate terms, the rod 12 is able to slide within the passage 52 and change in yaw, pitch, and roll at the first pivot point P1, while being constrained from side-to-side movement within the passage 52 at the first pivot point P1.

In some embodiments, the mounting portion 50 includes a stem 60 and a pedestal 62, the pedestal 62 having an central portion 64, a first anchor point 66, and a second anchor point 68, the central portion 64 extending between the first and second anchor points 66, 68 and each of the anchor points 66, 68 defining a surface suitable for mounting the first rod anchor 14A to one or more vertebrae 26. The first and second anchor points 66, 68 optionally include through holes 70, 72, respectively, for receiving a fastener (not shown), such as a pedicle screw or similar device to secure the mounting portion 50 to one or more vertebra 26, such as the first vertebra 26A (FIG. 1).

In some embodiments, the first rod anchor 14A is adapted, or otherwise structured, to limit pitch and yaw of the rod 12 to a predefined range. For example, the rod 12 is able to angulate within a range until opposing surfaces of the rod 12, contact, or bind with the upper and lower curves 56, 58 of the convex surface 54. In other words, a radius of curvature of the convex surface 54 is optionally selected to control a range of motion of the rod 12. In some embodiments, pitch and yaw of the rod 12 is limited to within an angular range Ra of about 60 degrees, for example. As subsequently described in association with the second rod anchor 14B, various means of limiting roll and/or sliding of the rod 12 within a predefined range are also contemplated.

Although in some embodiments the mounting portion 50 is adapted to receive one or more fasteners as shown in FIGS. 5*a* and 5*b*, FIG. 6 shows the first rod anchor 14A with the mounting portion 50 being adapted to act as a fastener, similar to that of a pedicle screw. Thus, the first rod anchor 14*a* optionally includes fastener means for securing the first anchor 14A to one of the vertebra 26.

Figure 7:
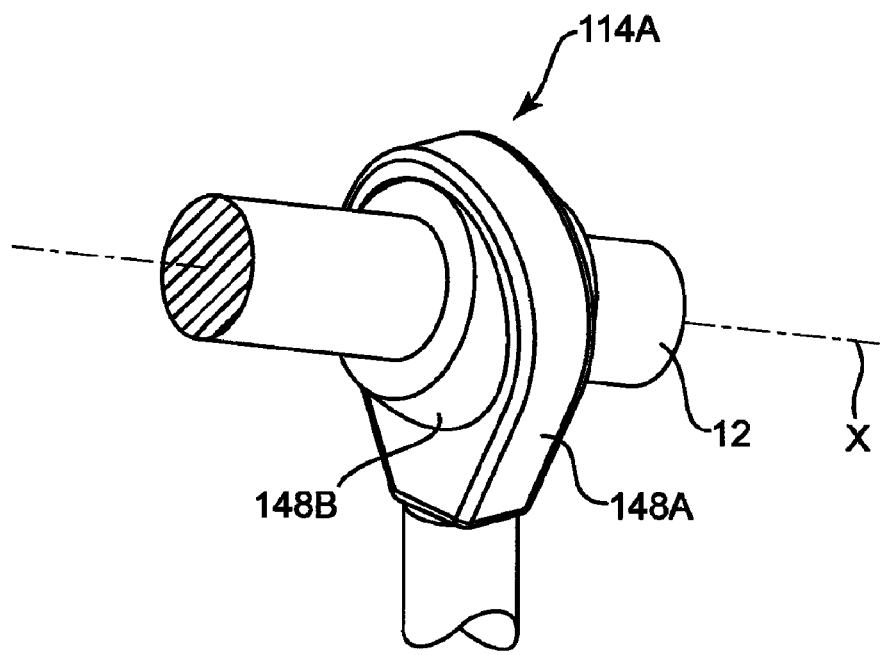
FIGS. 7 and 8 show features of another anchor of the system of FIG. 1, according to some embodiments.
Figure 8:
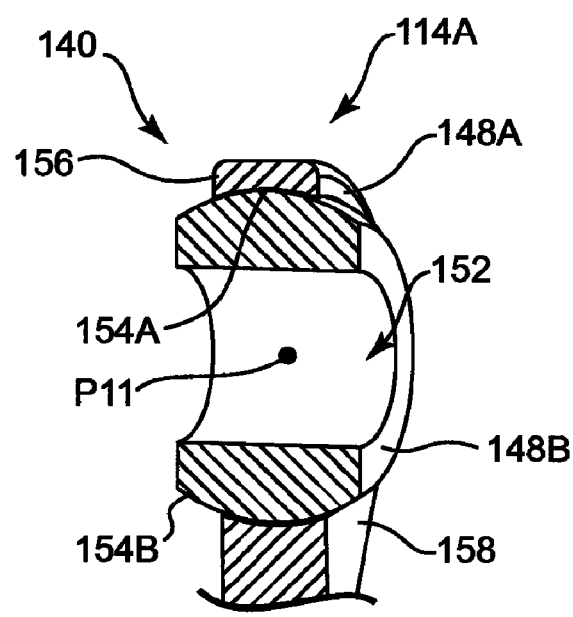

Although FIGS. 5*a*, 5*b*, and 6 are illustrative of some potential features the system 10, FIGS. 7 and 8 show a first rod anchor 114A according to some other embodiments, where FIG. 7 is a perspective view with the rod 12 received by the first rod anchor 114A and FIG. 8 is a cross-sectional view of the first rod anchor 114A with the rod 12 removed. The first rod anchor 114A is substantially similar to the first rod anchor 14A, although a housing 140 of the first rod anchor 114A includes a receptacle portion 148A and a sleeve portion 148B. In some embodiments, the sleeve portion 148B is substantially spherical in shape and the receptacle portion 148A forms a substantially spherical mating race for the sleeve portion 148B.

As shown in FIG. 8, the receptacle portion 148A has a revolute, substantially concave surface 154A and the sleeve portion 148B has a revolute, substantially convex surface 154B. The surfaces 154A, 154B are adapted, or otherwise structured, to form a substantially complementary fit with one another, such that the sleeve portion 148B is captured by the receptacle portion 148A and is allowed relative rotational and angular movement with respect to the receptacle portion 148A.

The sleeve portion 148B has a passage 152 defining a pivot point P11 through which the rod 12 is able to be slidably received. As with other embodiments, the complementary relationship between the sleeve portion 148B and the receptacle portion 148A is optionally designed to restrict, or limit, certain relative movement of the rod 12 with respect to the first rod anchor 114A. For example, in some embodiments, pitch and yaw of the rod 12 about the pivot point P11 is limited when opposing surfaces of the rod 12 contact the receptacle portion 148A proximate a front 156 and/or a back 158 of the receptacle portion 148A.

FIG. 9 is a perspective view of the second rod anchor 14B and FIGS. 10 and 11 are perspective views of portions thereof. The second rod anchor 14B is adapted to be fixed, and provides means for fixation to a second vertebra, such as a second vertebra 26B (FIG. 1). The second rod anchor 14B is further adapted to receive, and provides means for receiving the rod 12 (FIG. 1) such that the second rod anchor 14B limits translational movement of the rod 12 except along the longitudinal axis X and allows the rod 12 to change in at least pitch and yaw about a second pivot point P2. The second rod anchor 14B is optionally substantially similar to the first rod anchor 14A or first rod anchor 114A, including any desired combination of previously-described features.

The second rod anchor 14B is optionally formed of biocompatible metallic materials, such as titanium or stainless steel and/or biocompatible polymeric materials, such as PEEK. In some embodiments, and as shown in FIG. 9, the second rod anchor 14B includes a housing 200 having receptacle portion 202 and a sleeve portion 204 adapted to receive the rod 12, the second rod anchor 14B further including a mounting portion (e.g., similar to the mounting portion 50 of the first rod anchor 14A) adapted to secure the second rod anchor 14B to the second vertebra 26B.

The second rod anchor 14B is optionally adapted, or otherwise structured, to limit rotation, or roll, of the rod 12 about the longitudinal axis X of the rod 12 (FIG. 3). In particular, the second rod anchor 14B provides means for allowing the rod 12 to angulate without substantial lateral translation relative to the second rod anchor 14B or substantial rotation about the longitudinal axis X. The sleeve portion 204 is optionally spherical in shape and the receptacle portion 202 forms a substantially spherical mating race, where rotation of the sleeve portion 204 relative to the receptacle portion 202 is substantially inhibited in at least one plane.

FIG. 10 shows the receptacle portion 202 and FIG. 11 shows the sleeve portion 204, where the receptacle portion 202 has a revolute, substantially concave inner surface 210 and the sleeve portion 204 has a revolute, substantially convex outer surface 212. The surfaces 210, 212 are adapted to form a substantially complementary fit with one another, such that the sleeve portion 204 is captured by the receptacle portion 202 and is allowed relative angular movement with respect to the receptacle portion 202.

As shown in FIG. 10, the receptacle portion 202 also includes a pair of protrusions 216 (e.g., pins), extending inwardly from and at opposite sides of the inner surface 210. In turn, as shown in FIG. 11, the sleeve portion 204 has a circumferential groove 218 adapted to slidably receive the protrusions 216 and an internal passage 220 through which the rod 12 is able to be slidably received. A pivot point P2 is also defined in the passage 220, the rod 12 passing through the pivot point P2.

The passage 220 optionally has a non-circular cross-section (e.g., a substantially D-shaped cross-section corresponding to the second section 32 of the rod 12). Upon mating the non-circular cross-sections of the rod 12 and the passage 220, rotation of the rod 12 relative to the sleeve portion 204 is substantially inhibited.

Upon slidably receiving the protrusions 216 in the circumferential groove 218 the pitch and yaw of the rod 12 are able to change. Relative rotation between the sleeve portion 204 and the receptacle portion 202, however, is substantially inhibited. Thus, as relative rotation between the sleeve portion 204 and the receptacle portion 202 is also substantially inhibited, relative rotation between the rod 12 and the second rod anchor 14B is substantially inhibited or limited, allowing the rod 12 to be maintained at a pre-selected rotational position relative to the second rod anchor 14B. It also should be understood that other cross-sectional shapes for each of the passage 220 and rod 12 can be selected to allow some degree of rotation about the longitudinal axis X within a predefined range, including, for example, that shown in FIG. 12, where the rod 12 is shown with features allowing rotation up to a stop 220A formed by the sleeve 204. The cross-sectional shape of the rod 12 is also optionally selected to limit axial translation of the rod 12 as desired.

As with other embodiments, the second rod anchor 14B is also optionally adapted to restrict, or limit angulation of the rod 12 (e.g., pitch and yaw) with respect to the second rod anchor 14B. For example, pitch and yaw of the rod 12 about the pivot point P2 is limited when the rod 12 contacts the receptacle portion 202 proximate a front 222 and/or a back 224 of the receptacle portion 202. A size and shape of the receptacle and/or sleeve portions 202, 204 is selected to define such limit(s) as desired.

Figure 13:
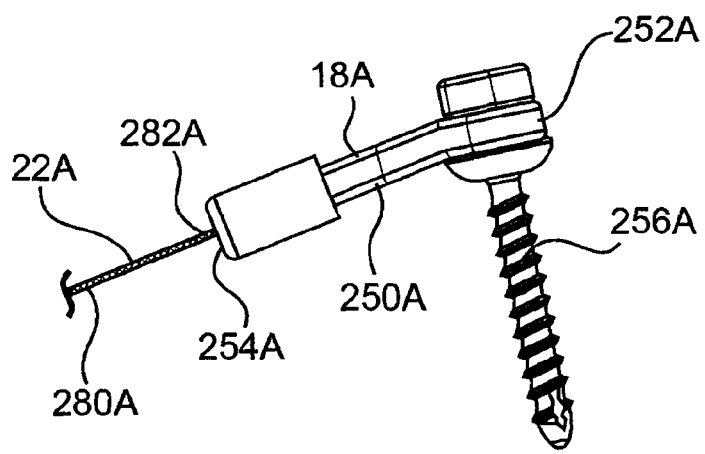
FIG. 13 shows a vertebral anchor and first force directing member of the system of FIG. 1, according to some embodiments.

FIG. 13 shows the first vertebral anchor 18A and first force directing member 22A from a front elevation view. The first vertebral anchor 18A, also described as an anchor arm, is adapted to be fixed, and provides means for fixation, to a third vertebra 26C (FIG. 1). As previously described, the first vertebral anchor 18A is fixed to a portion of the spinal column 24 (FIG. 1) having an abnormal curvature in need of correction.

The first and second vertebral anchors 18A, 18B are optionally substantially similar, and thus various features of both the first and second vertebral anchors 18A, 18B are described in association with the first vertebral anchor 18A, where when referenced, features of the first vertebral anchor 18A are designated with reference numbers followed by an "A" and similar features of the second vertebral anchor 18B are designated with similar reference numbers followed by a "B."

The first vertebral anchor 18A includes an arm 250A and a head 252A. In some embodiments, the arm 250A extends from the head 252A to a terminal end 254A and is disposed generally perpendicular to the head 252A. The arm 250A is optionally rotatable relative to the head 252B and is adapted to extend across a portion of the third vertebra 26C, for example, from one side of the spinal column 24 to an opposite side of the spinal column 24. For example, the first vertebral anchor 18A is secured to the third vertebra 26C such that the arm 250A extends across the third vertebra 26C through a hole or hollowed portion in the spinous processes (not shown) of the third vertebra 26C.

The head 252A is adapted, or is otherwise structured, to be fixed to a portion of the third vertebra 26C, such as a pedicle of the third vertebra 26C. The head 252A optionally includes and/or is adapted to work in conjunction with any of a variety of structures capable of engaging the third vertebra 26C. For example, the first vertebral anchor 18A optionally includes a pedicle screw 256A secured through the head 252A to a pedicle of the third vertebra 26C.

The first force directing member 22A is secured to the first vertebral anchor 18A at an appropriate location on the first vertebral anchor 18A. For example, in some embodiments the first force directing member 22A is secured to the first vertebral anchor 18A at least at the terminal end 254A of the arm 250A such that the first force directing member 22A extends from the terminal end 254A of the arm 250A.

Additional examples of vertebral anchors (also described as "implants") in accordance with some embodiments of the system 10 are set forth in U.S. application Ser. No. 11/196, 952, filed on Aug. 3, 2005 and entitled DEVICE AND METHOD FOR CORRECTING A SPINAL DEFORMITY, as well as Ser. No. 12/134,058, filed on Jun. 5, 2008 and entitled MEDICAL DEVICE AND METHOD TO CORRECT DEFORMITY, the entire contents of both of which are hereby incorporated by reference.

Figure 14A:
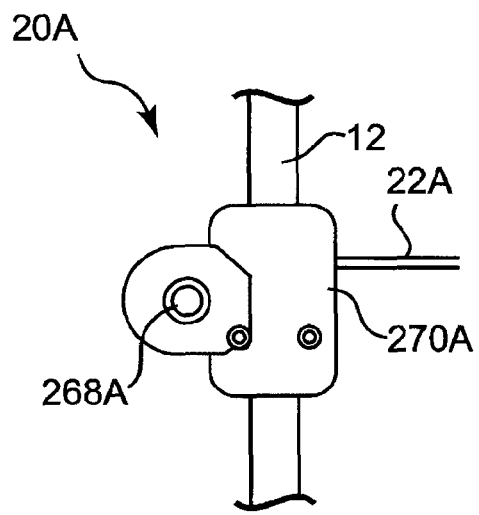
FIGS. 14a and 14b show an adjustment mechanism of the system of FIG. 1, according to some embodiments.
Figure 14B:
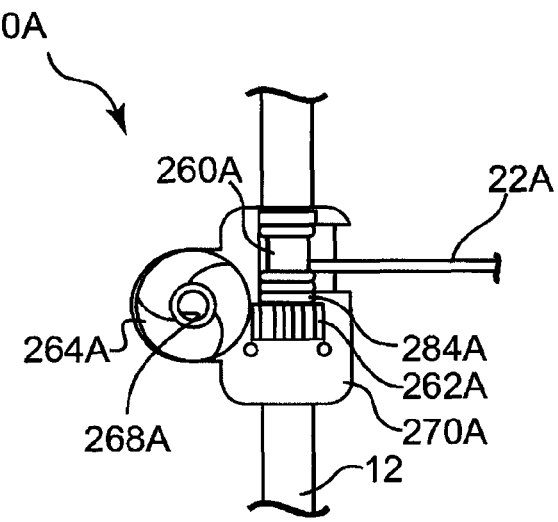

FIGS. 14a and 14b show the first adjustment mechanism 20A, where FIG. 14b shows the first adjustment mechanism 20A with a portion removed to illustrate inner features thereof. In some embodiments, the first adjustment mechanism 20A provides means for securing the first force directing member 22A to the rod 12. In some embodiments, the first adjustment mechanism 20A, also described as a tensioner or coupler, is further adapted to adjust, and provides means for adjusting a length of the first force directing member 22A. The first and second adjustment mechanisms 20A, 20B are optionally substantially similar. Thus, various features of both the first and second adjustment mechanisms 20A, 20B are described in association with the first adjustment mechanism 20A, where features of the first adjustment mechanism 20A are designated with reference numbers followed by an "A" and similar features of the second adjustment mechanism 20B are designated with the same reference numbers followed by a "B."

In some embodiments, the first adjustment mechanism 20A includes a reel 260A, a circumferential gear 262A surrounding the reel 260A, a vertical gear 264A in contact with the circumferential gear 262A, an actuation head 268A, and a housing 270A.

The reel 260A, as well as the circumferential gear 260A and vertical gear 264A are maintained at least partially within the housing 270A. In turn, the housing 270A is adapted to be secured to the rod 12. For example, the housing 270A optionally forms a central lumen through which the rod 12 is receivable. Upon inserting the rod 12 through the central lumen, the housing 270A is adapted to be clamped onto the rod 12.

In some embodiments, the housing 270A incorporates a clamshell design (e.g., a first portion adjustably secured to a second portion) adapted to be tightened onto the rod 12 (e.g., using one or more fasteners). Thus, in some embodiments, the first adjustment mechanism 20A is substantially fixed with respect to the rod 12. In other embodiments, however, the first adjustment mechanism 20A is movable with respect to the rod 12, for example being able to rotate about the rod 12.

The first force directing member 22A is attached or secured to the reel 260A and passes out of the housing 270A through an appropriately sized opening in the housing 270A. Actuation of the vertical gear 264A via the actuation head 266A turns the circumferential gear 262A, which turns the reel 260A, thus winding (or unwinding, depending on the direction in which the reel 260A is turned) the first force directing member 22A about the reel 260A. Rotation of the reel 260A in the appropriate direction draws the first force directing member 22A in toward the first adjustment mechanism 20A, pulling the first vertebral anchor 18A (FIG. 13) toward the first adjustment mechanism 20A according to some methods of correcting a spinal defect.

Additional examples of adjustment members (also described as "adjustment mechanisms"), in accordance with some embodiments of the system 10 are set forth in U.S. application Ser. No. 11/196,952, filed on Aug. 3, 2005 and entitled DEVICE AND METHOD FOR CORRECTING A SPINAL DEFORMITY, as well as Ser. No. 12/134,058, filed on Jun. 5, 2008 and entitled MEDICAL DEVICE AND METHOD TO CORRECT DEFORMITY, the entire contents of both of which are hereby incorporated by reference.

As shown in FIGS. 13 and 14, the first and second force directing members 22A, 22B are optionally substantially similar, and thus various features of both the first and second force directing members 22A, 22B are described in association with the first force directing member 22A, where features of the first force directing member 22A are designated with reference numbers followed by an "A" and similar features of the second force directing member 22B are designated with similar reference numbers followed by a "B."

In some embodiments, the first force directing member 22A is substantially flexible such that the first force directing member 22A is able to be pivoted in a multiple directions and/or be spooled or wound, for example. Suitable flexible materials for forming the first force directing member 22A include wire and stranded cables, monofilament polymer materials, multifilament polymer materials, multifilament carbon or ceramic fibers, and others. In some embodiments, the first force directing member 22A is formed of stainless steel or titanium wire or cable, although a variety of materials are contemplated.

The first force directing member 22A, also described as a connector or cable, is adapted to be secured to the first vertebral anchor 18A and the first adjustment member 20A, the force directing member 22A defining an effective length between the first adjustment mechanism 20A and the first vertebral anchor 18A, and thus the rod 12 (although, in some embodiments, the first force directing member 22A is secured directly to the rod 12). As described, in some embodiments, the first adjustment mechanism 20A is adapted to modify, and provides means for modifying, the effective length of the force directing member 22A. The first force directing member 22A has a body 280A and extends from a first end 282A to a second end 284A.

FIG. 1 shows the assembled system 10. In some embodiments, assembly of the system 10 includes securing the first and second force directing members 22A, 22B to the first and second vertebral anchors 18A, 18B, respectively. The first and second force directing members 22A, 22B are also secured to the first and second adjustment mechanisms 20A, 20B. The first and second adjustment mechanisms 20A, 20B are secured to the rod 12. The first and second rod anchors 14A, 14B are secured to the first and second vertebrae 26A, 26B, respectively. The rod 12 is received in the first and second rod anchors 14A, 14B to secure the rod 12 against lateral translation relative to the spinal column 24. The first and second vertebral anchors 18A, 18B are secured to the third and fourth vertebrae 26C, 26D. Upon assembly of the system 10, the first and second adjustment mechanisms 20A, 20B are adjusted as desired to pull the first and second vertebral anchors 18A, 18B toward the first and second adjustment mechanisms 20A, 20B, and thus the rod 12.

The first force directing member 22A is assembled to the first vertebral anchor 18A by securing the first end 282A of the first force directing member 22A to the first vertebral anchor 18A proximate the terminal end 254A thereof. In some embodiments, the first force directing member 22A is secured at the terminal end 254A of the first vertebral anchor 18A, and extends along at least a portion of the arm 250A to the head 252A, although the first force directing member 22A is attached at any location along the arm 250A and/or the head 252A of the first vertebral anchor 18A as appropriate. The first force directing member 22A is securable to the first vertebral anchor 18A via a variety of methods, including welding, adhesives, tying, and/or screw fixation, for example.

The second force directing member 22B and the second vertebral anchor 18B are optionally secured or connected together using similar approaches.

As previously described, the first force directing member 22A extends to the first adjustment mechanism 20A, enters the housing 250A, and is wound about the reel 260A, thereby coupling the first adjustment mechanism 20A to the first vertebral anchor 18A as well as the rod 12. In some embodiments, the first force directing member 22A is secured to the reel 260A via welding, screw fixation, adhesives, and/or is sufficiently wound about the reel 260A for frictional retention of the first force directing member 22A on the reel 260A.

The second force directing member 22A and the second adjustment mechanism 20B are optionally secured or connected together using similar approaches.

The rod 12 is received by the housings 40, 200 of the first and second rod anchors 14A, 14B, respectively. Features of the first and second rod anchors 14A, 14B are selected to limit pitch, yaw, roll, and axial sliding of the rod 12 as desired.

The rod 12 is secured against lateral translation relative to the longitudinal axis of the spinal column 14 by securing the first and second rod anchors 14A, 14B to at least the first and second vertebra 26A, 26B, respectively. The first rod anchor 14A is secured to at least the first vertebra 26A, for example by screwing the first rod anchor 14A to the first vertebra 26A (e.g., at or near the transverse processes) using one or more pedicle screws. The second rod anchor 14B is similarly secured to at least the second vertebra 26B. The first rod anchor 14A and/or the second rod anchor 14B are optionally secured to multiple vertebrae 26 for enhanced stability.

In some embodiments, the rod 12 is attached by the rod anchors 14A, 14B to transverse processes on the left side of the spinal column 24 and is able to slide axially relative to the first and/or second rod anchors 14A, 14B. In other embodiments, the rod 12 is attached by the rod anchors 14A, 14B to the right side of the spinal column 24, on different sides of the spinal column 24 (e.g., the first rod anchor 14A on the left side and the second rod anchor 14B on the right side), or along the mid-line of the spinal column 24. In other embodiments, the rod 12 is adjustable length to compensate for changes in length of the spinal column 24. Regardless, the interaction between the rod 12 and the first and second rod anchors 14A, 14B helps facilitate growth and more natural movement of the spinal column 24.

Figure 15A:
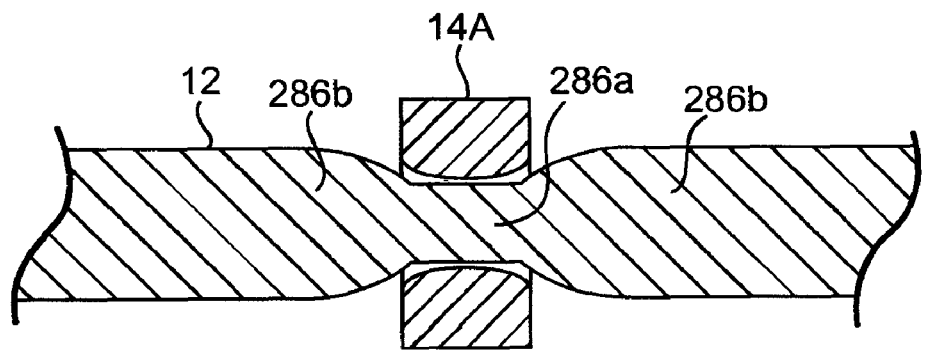
FIGS. 15a, 15b, and 15c show some stop features of the system of FIG. 1, according to some embodiments.
Figure 15B:
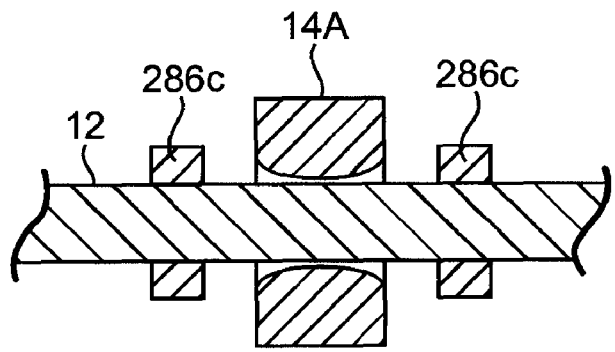
Figure 15C:
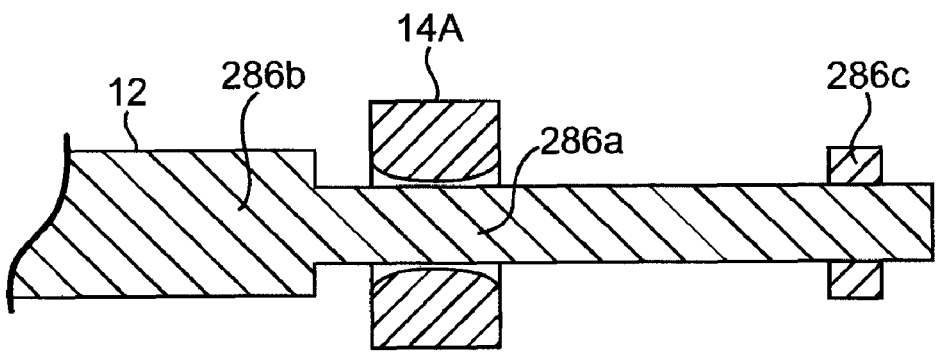

FIGS. 15a, 15b, and 15c show various stop features 286 for limiting axial sliding, or translation of the rod 12 relative to a rod anchor, such as the first rod anchor 14A. Generally, sliding of the rod 12 in a particular axial direction is substantially limited, or arrested, when a stop feature 286 engages, or abuts an adjacent rod anchor 14.

As shown in FIG. 15a, the rod 12 optionally includes a narrowed portion 286a received in the first rod anchor 14A with wider, adjacent portions 286b of the rod 12 limiting axial sliding of the rod 12. As shown, although axial sliding of the rod 12 is substantially prevented by locating the stop features 286 adjacent the first rod anchor 14A, there is still some tolerance allowed, or play, as appropriate in the fit between the wider portions 286b of the rod 12 and the first rod anchor 14A.

As shown in FIG. 15b, the system 10 optionally includes stops 286c, or collars, that are fit onto the rod 12 adjacent the first rod anchor 14A to substantially limit axial sliding of the rod 12 within the first rod anchor 14A. In some embodiments, the stops 286c are metal or polymeric collars crimped onto the rod 12, although a variety of designs and methods of securing are employed as desired. As shown, although axial sliding of the rod 12 is substantially prevented with respect to the first rod anchor 14A, there is still some limited play or slop as appropriate in the fit between the rod 12 and the stops 286c.

As shown in FIG. 15c, the system 10 optionally utilizes both a stop 286c and a narrowed portion 286a with a wider portion 286b to limit axial sliding of the rod 12 relative to the first rod anchor 14A within a desired range of motion. For example, as shown in FIG. 15c, the stop 286c is located toward an end of the rod 12 on one side of the first rod anchor 14A and the wider portion 286b is located on the other side of the first rod anchor 14A with a desired spacing between the stop 286c and the wider portion 286b. Any combination of stop features 286 and spacing are implemented as appropriate.

Figure 16:
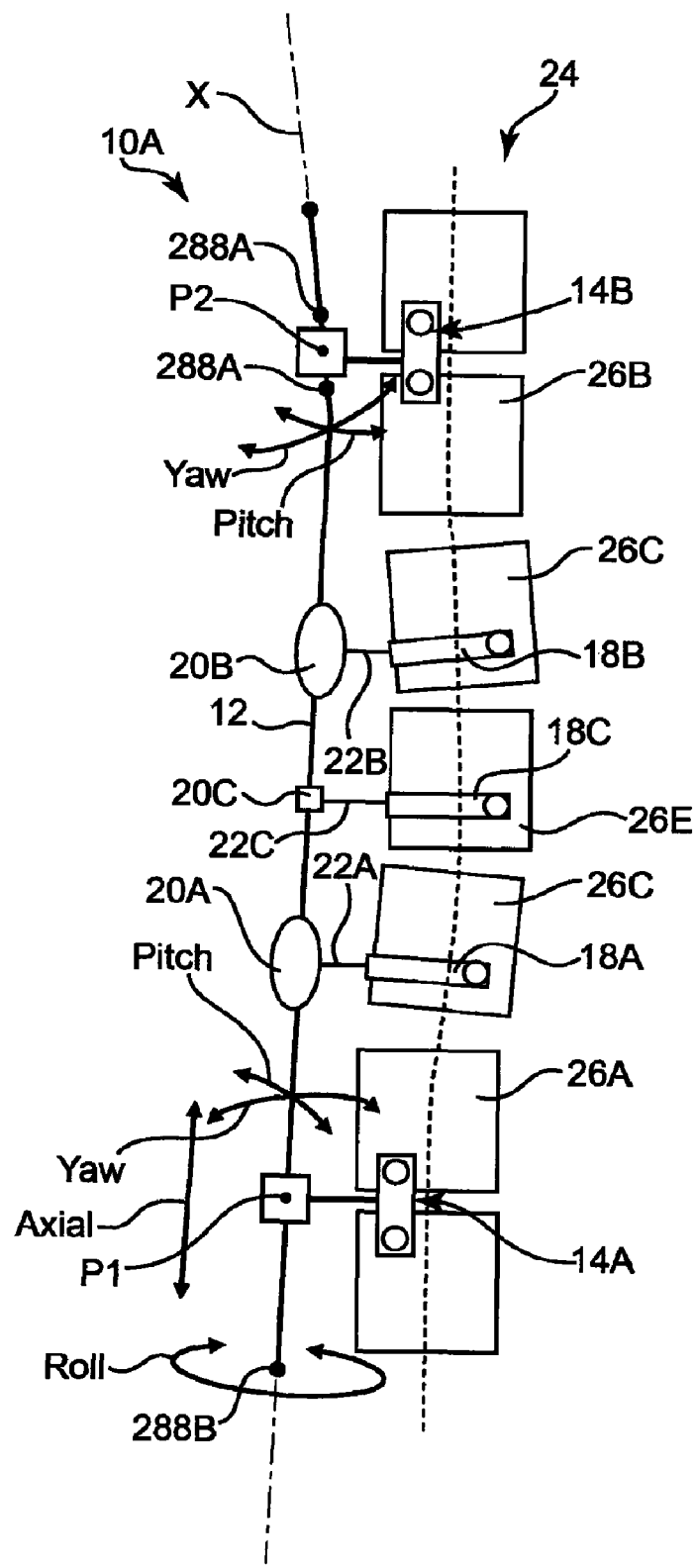
FIG. 16 is a diagrammatical view showing some of the degrees of freedom of the system of FIG. 1, according to some embodiments.

FIG. 16 is a diagrammatical view of a system 10A similar to that of FIG. 1, where FIG. 16 illustrates various degrees of freedom of the rod 12 at the first and second rod anchors 14A, 14B, according to some embodiments. As shown, the system 10A further includes a third vertebral anchor 18C secured to a fifth vertebra 26D. The third vertebral anchor is substantially similar to the first and/or second vertebral anchors 18A, 18B. The system 10 also optionally includes a corresponding third force directing member 22C, e.g., a cable or wire, and a third adjustment mechanism 20C. Although adjustment mechanisms 20 including means for adjusting the effective length of the force directing members 22 have been described, in some embodiments one or more of the adjustment mechanisms 20 acts as a means for coupling a corresponding force directing member to the rod 12 without incorporating such adjustment features. For example, the third adjustment mechanism 20C, or any of the adjustment mechanisms described herein, is optionally a crimp or fastener means for securing the force directing member 22C to the rod 12 (e.g., a clamp or crimp).

The rod 12 is bent (e.g., as shown in FIG. 3) and, as designated by the directional arrows, is free to change in pitch, yaw, and roll, as well as to slide axially along the longitudinal axis X at the first rod anchor 14A (and thus, at the first pivot point P1) and is free to change in pitch and yaw at the second rod anchor 14B while relative changes in roll and axial sliding are substantially limited or substantially prevented at the second rod anchor 14B (and thus, at the second pivot point P2). In some embodiments, collars 288A or other stop features (such as those previously described) are located on the rod 12 (e.g., crimped onto the rod 12) on either side of the second rod anchor 14B in order to inhibit sliding movement of the rod 12. In turn, a stop feature 288B (such as one of those previously described) is located proximate a terminus of the rod 12 in order to help prevent the rod 12 from slipping off the first rod anchor 14A.

The interaction between the vertebral anchors 18A, 18B, adjustment mechanisms 20A, 20B, and in particular the flexible nature of their respective coupling through use of the force directing members 22A, 22B allows the system 10 to move dynamically with the spinal column 24, while exerting and/or maintaining a corrective force (e.g., lateral and derotational forces) on the third and fourth vertebrae 26C, 26D. In other words, the system 10 is semi-constrained, providing a lateral and derotational anchor point while facilitating at least some degree of natural movement in the spinal column 24.

Moreover, by limiting rotation, or roll, of the rod 12, the bend in the rod 12 is oriented and maintained in a desired rotational position. Maintaining the rotational orientation at one end (i.e., at the second rod anchor 14B) is useful, for example, to help ensure that the bend or shape of the rod 12 consistently follows or otherwise appropriately tracks a desired curvature of a spinal column 24. Freedom of rotation at the other end of the rod 12 (i.e., at the first rod anchor 14A), however, still permits the spinal column 24 to have more natural movement while the corrective forces are being applied.

Thus, according to various embodiments, the spinal column 24 (and thus, the person) is able to twist, bend side-to-side, and bend forward-and-backward in a more natural manner while corrective forces are being applied to the spinal column 24. In some embodiments, the effective lengths of the force directing members 22A, 22B are adjusted (e.g., periodically or all at one time), bringing the spinal column into natural alignment, while the system 10 still facilitates a more natural movement of the spinal column 24 (e.g., twisting and bending forward-and-backward and side-to-side) due to the freedom of movement afforded by the system 10.

Figure 17:
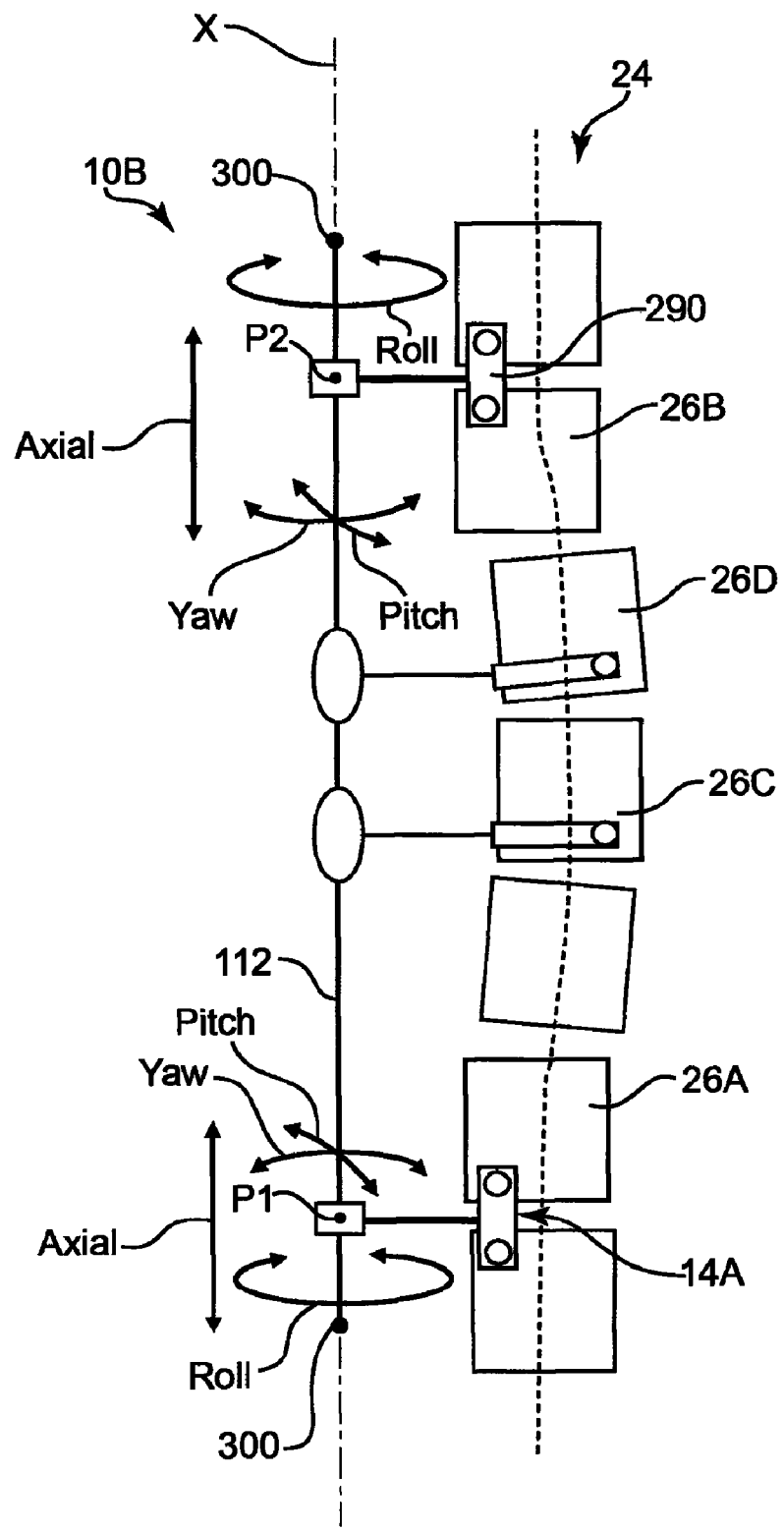
FIG. 17 is another diagrammatical view showing some other degrees of freedom of the system of FIG. 1, according to some embodiments.

FIG. 17 is a diagrammatical view of a system 10B illustrating various degrees of freedom of the rod 112 at the first rod anchor 14A and a second rod anchor 290 substantially similar to the first rod anchor 14A, according to some other embodiments of the system 10. With the system 10B, the rod 112 is substantially straight (FIG. 4) and, as designated by the directional arrows, is free to change in pitch, yaw, and roll, as well as to slide axially along the longitudinal axis X, at each of the first and second rod anchors 14A, 290.

In some embodiments, each of the first and second rod anchors 14A, 290 shown generally in FIG. 16 are substantially the same as the first rod anchor 14A shown in FIGS. 5a and 5b, for example. In other embodiments, each of the first and second rod anchors 14A, 290 are substantially the same as the first rod anchor 114A shown in FIGS. 7 and 8, although any combination of the previously-described anchor features described in association with any of the rod anchors 14A, 114A, 14B are contemplated.

The rod 112 also optionally includes stop features 300, such as the stop features 286 previously described, to help prevent the rod 112 from slipping out of the first and second rod anchors 14A, 290. In this manner, the rod 112 is able to slide axially, along the longitudinal axis X (FIG. 4) until one of the stop features 300 contacts one of the first and second rod anchors 14A, 290. Once again, the system 10B provides dynamic adjustment and movement with the spine, while exerting a corrective force (e.g., translational and derotational forces) on the vertebrae 26 (e.g., the third and fourth vertebrae 24C, 24D).

Figure 18:
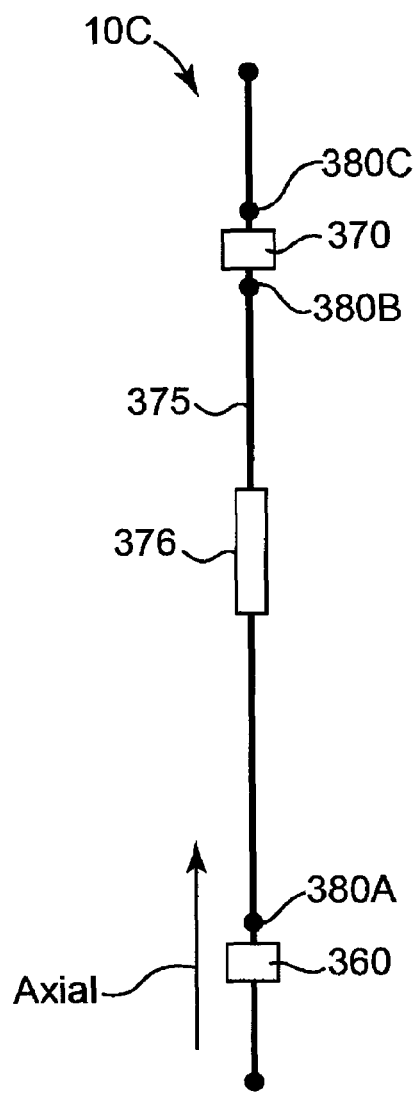
FIGS. 18 and 19 are other diagrammatical views showing axial translation degrees of freedom, according to some embodiments.
Figure 19:
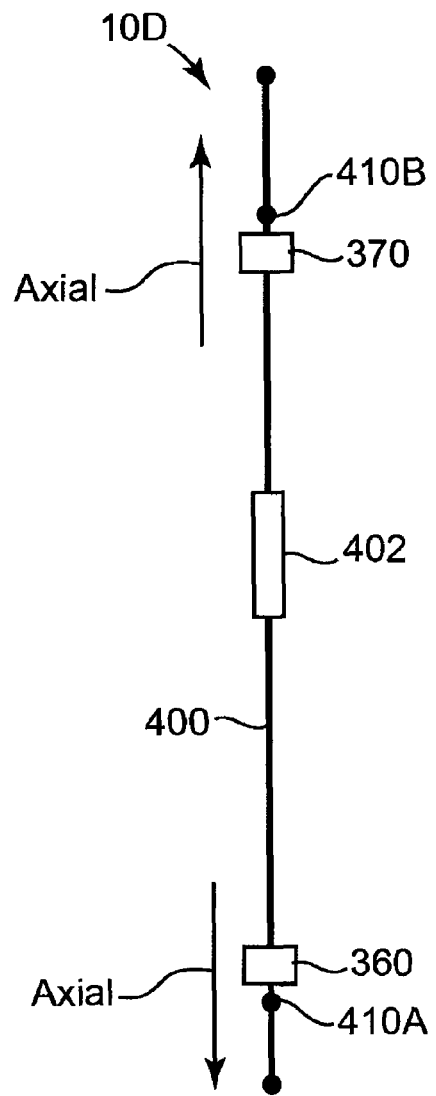

FIGS. 18 and 19 show systems 10C, 10D, respectively, demonstrating variations in axial rod constraint according to some embodiments. The systems 10C, 10D are each shown including a first rod anchor 360 and a second rod anchor 370 which incorporate features of any of the anchors previously described. The axial arrows indicate freedom of movement of the associated rods, although a designation of degrees of freedom in pitch, yaw, and roll at the anchors 360, 370 are left from FIGS. 18 and 19 for ease of illustration. Various degrees of freedom at the anchors 360, 370 are incorporated as appropriate.

As shown in FIG. 18, the system 10C includes a rod 375 (e.g., similar to the rod 12A) including a rod adjustment mechanism 376 (e.g., similar to the rod adjustment mechanism 39), a first stop feature 380A, a second stop feature 380B, and a third stop feature 380C, the stop features 380A, 380B, 380C being secured to and/or formed with the rod 375 (e.g., similar to the stop features being similar to any of the stop features 286 previously described).

The rod 375 is substantially constrained against axial sliding by the second and third stop features 380B, 380C at the second rod anchor 370 and is allowed some axial sliding, or axial translation, outwardly away from the first stop feature 380A. In some embodiments, the stop features 286 and the first and second rod anchors 360, 370 provide means for imposing a distraction force on the spinal column 24 and/or for limiting compression of the spinal column 24 along one or more sides of the spinal column 24 (e.g., left, right, anterior, and/or posterior sides).

In some embodiments, the rod adjustment mechanism 376 is used to apply a distraction force by expanding an effective length of the rod 375 such that the first and second stop features 380A, 380B engage the first and second rod anchors 360, 370 resulting in a compressive force on the rod 375 that the rod 375 substantially rigidly resists. The compressive force on the rod 375, in turn, results in a distraction, or elongation force on a side of the spinal column 24 to which the anchors 360, 370 of the system 10C are coupled. Moreover, the stop features additionally or alternatively provide a limit on compression of the spinal column 24 at the first side of the spinal column 24 by limiting relative movement of the anchors 36, 370 toward one another on the rod 375.

Although the rod 375 of the system 10C is placed under a compressive load, the rod 375 is able to move axially in a first direction, e.g., to allow further distraction and/or natural movement—e.g., such that the spinal column 24 (and thus, the person) is able to twist, bend side-to-side, and bend forward-and-backward in a more natural manner while distractive forces are being applied to the spinal column 24. In turn, axial movement of the rod 375 in a second direction generally opposite the first direction is limited (e.g., thereby limiting compression of the spinal column 24 beyond the axial limit set by the stop features 286). Moreover, although the system 10C is described as applying a distraction force and/or compressive limit to one side of the spinal column 24, in other embodiments a distraction force is applied to both sides of the spinal column 24, to an anterior side of the spinal column 24, to a posterior side of the spinal column 24, or combinations thereof.

As shown in FIG. 19, the system 10D includes a rod 400 (e.g., similar to the rod 12A) including a rod adjustment mechanism 402 (e.g., similar to rod adjustment mechanism 39), a first stop feature 410A and a second stop feature 410B, the stop features 410A, 410B being secured to and/or formed with the rod 400 (e.g., similar to any of the stop features 286 previously described). The rod 400 is substantially constrained against axial sliding and/or outward expansion by the first and second stop features 410A, 410B, the stop features 41A, 410B providing means for imposing a compressive force on the spinal column 24 and/or for limiting distraction of the spinal column 24 along one or more sides of the spinal column 24 (e.g., left, right, anterior, and/or posterior sides). In some embodiments, the rod adjustment mechanism 402 is used to apply a contraction or tensioning force on the spinal column to which the system 10D is coupled by contracting or shortening the rod 400 using the adjustment mechanism 402 such that the first and second stop features 410A, 410B engage the first and second rod anchors 360, 370 to apply a compressive force to the spinal column (not shown).

Although the rod 400 of the system 10D is placed under a tensile load, the rod 400 is able to move axially in a first direction, for example, to allow further compression of the spinal column 24 (and thus, the person) is able to twist, bend side-to-side, and bend forward-and-backward in a more natural manner while compressive forces are being applied to the spinal column 24. Axial movement of the rod 400 is still substantially limited in a second direction generally opposite the first direction, for example, limiting distraction of the spinal column 24 beyond the axial limit set by the stop features 286. Moreover, although the system 10D is described as applying a compressive force and/or distraction limit to one side of the spinal column 24, in other embodiments a tensile, or compressive force is applied to both sides of the spinal column 24, to an anterior side of the spinal column 24, to a posterior side of the spinal column 24, or combinations thereof. In further embodiments, the system 10D can apply a compressive force and/or distraction limit to one side of the spinal column 24, while the system 10C applies a distraction force and/or compression limit to the opposite side of the spinal column 24.

In view of the foregoing, systems, methods, and devices according to the various embodiments provided herein help minimize a number of anchor points utilized for correction, facilitate use of straight or contoured rods, and/or help promote a more natural, physiologic motion of the spinal column 24 during or after correction of the deformity.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for correcting a spinal deformity, the system comprising:
   a rod adapted to extend along a spine of a patient;
   a first rod anchor adapted to be fixed to a first vertebra of the spine, the first rod anchor receiving the rod such that the rod is secured against substantial lateral translation relative to the first rod anchor and the rod is allowed to slide axially relative to the first rod anchor through a first pivot point and to change in at least two of pitch, yaw, and roll about the first pivot point;
   a second rod anchor adapted to be fixed to a second vertebra, the second rod anchor receiving the rod such that the rod is secured against substantial lateral translation relative to the second rod anchor and is allowed to change in at least pitch and yaw about a second pivot point;
   a first vertebral anchor adapted to be fixed to a third vertebra;
   a first adjustment mechanism; and
   a first force directing member coupled to the first vertebral anchor and the rod, the first force directing member defining an effective length between the first vertebral anchor and the rod, the first adjustment mechanism being adapted to modify the effective length of the force directing member.

2. The system of claim 1, wherein the first rod anchor is further adapted to limit pitch of the rod relative to the first rod anchor to a predefined range.

3. The system of claim 1, wherein the first rod anchor is further adapted to limit yaw of the rod relative to the first rod anchor to a predefined range.

4. The system of claim 1, wherein the first rod anchor is further adapted to limit roll of the rod relative to the first rod anchor to a predefined range.

5. The system of claim 1, wherein the system limits axial sliding of the rod relative to the first rod anchor to a predefined range.

6. The system of claim 1, wherein the second rod anchor is further adapted to allow roll of the rod about the second pivot point.

7. The system of claim 1, wherein the second rod anchor is further adapted to substantially prevent roll of the rod about the second pivot point.

8. The system of claim 1, wherein the second rod anchor is adapted to substantially prevent axial sliding of the rod relative to the second rod anchor.

9. The system of claim 1, wherein the rod defines a central portion extending between the first and second rod anchors and further wherein the central portion is substantially straight.

10. The system of claim 1, wherein the rod defines a central portion extending between the first and second rod anchors and further wherein the central portion is substantially non-linear.

11. The system of claim 1, wherein the rod defines a central portion extending between the first and second rod anchors and further wherein the central portion includes a substantially curved section and a substantially straight section.

12. The system of claim 1, wherein the first rod anchor comprises:
    a housing forming a receptacle portion having a substantially concave surface; and
    a sleeve slidably receiving the rod and having a substantially convex mating surface adapted to mate with the concave surface of the housing such that the sleeve is adapted to rotate relative to the housing to change in pitch and yaw.

13. The system of claim 1, wherein the first rod anchor comprises a housing forming a passage defining a revolute convex surface receiving the rod.

14. The system of claim 1, wherein the rod defines a chase feature and the second rod anchor comprises:
    a housing forming a receptacle portion having a substantially concave surface; and
    a sleeve forming a chase slidably receiving the chase feature of the rod to substantially inhibit roll of the rod in the sleeve, the sleeve having a substantially convex mating surface adapted to mate with the concave surface of the housing such that the sleeve is adapted to rotate relative to the housing to change in pitch and yaw.

15. The system of claim 14, wherein the second rod anchor further comprises a pair of projections between the housing and the sleeve, the sleeve including a circumferential groove receiving the pair of projections such that the sleeve is able to change in pitch in yaw relative to the housing and is substantially prevented from changing in roll relative to the housing.

16. A method of correcting a spinal deformity, the method comprising:
    securing a first rod anchor to a first vertebra of the spine and a second rod anchor to a second vertebra of the spine;
    slidably receiving a rod through a first pivot point in the first rod anchor and receiving the rod through a second pivot point in the second rod anchor, such that the rod is free to rotate and change in pitch and yaw about the first pivot point;
    securing a first vertebral anchor to a third vertebra;
    coupling a first force directing member to the first vertebral anchor and the rod;
    connecting the first force directing member to the first adjustment mechanism; and
    adjusting an effective length of the first force directing member with the first adjustment mechanism to help correct a spinal deformity.

17. The method of claim 16, further comprising allowing axial movement of the rod with respect to the first rod anchor.

18. The method of claim 16, further comprising winding the first force directing member using the first adjustment mechanism to shorten the effective length of the first force directing member.

19. A system for correcting a spinal defect, the system comprising:
- means for securing a rod to a first vertebra of a spine such that the rod is able to slide axially through a first pivot point defined by the means for securing the rod to the first vertebra and to change in pitch, yaw, and roll about the first pivot point;
- means for securing the rod to a second vertebra of a spine such that the rod is able to change in at least pitch and yaw about a second pivot point defined by the means for securing the rod to the second vertebra;
- means for anchoring to a third vertebra;
- a connector coupled to the rod and the means for anchoring to the third vertebra; and
- means for adjusting an effective length of the connector.

20. A system for correcting a spinal deformity located between a first vertebra and a second vertebra of a person's spine, the system comprising:
- a substantially rigid rod adapted to extend across the spinal deformity;
- a first rod anchor adapted to be fixed to the first vertebra and to receive a first end of the rod such that the rod is allowed to translate axially relative to the first rod anchor;
- a second rod anchor adapted to be fixed to the second vertebra and to receive a second end of the rod; and
- a first force directing member coupled between the rod and the spinal deformity;

wherein the first and second rod anchors are adapted to resist lateral translation of the rod relative to the spine and to allow a longitudinal axis of the rod to change in at least a pitch and a yaw.

21. A system for correcting a spinal deformity, the system comprising:
- a rod adapted to extend along a spine of a patient, the rod defining a central portion that is substantially non-linear;
- a first rod anchor adapted to be fixed to a first vertebra of the spine, the first rod anchor receiving the rod such that the rod is secured against substantial lateral translation relative to the first rod anchor and the rod is allowed to slide axially relative to the first rod anchor through a first pivot point and to change in at least two of pitch, yaw, and roll about the first pivot point;
- a second rod anchor adapted to be fixed to a second vertebra, the second rod anchor receiving the rod such that the rod is secured against substantial lateral translation relative to the second rod anchor and is allowed to change in at least pitch and yaw about a second pivot point, the central portion of the rod extending between the first and second rod anchors;
- a first vertebral anchor adapted to be fixed to a third vertebra;
- a first adjustment mechanism; and
- a first force directing member coupled to the first vertebral anchor and the rod, the first force directing member defining an effective length between the first vertebral anchor and the rod, the first adjustment mechanism being adapted to modify the effective length of the force directing member.

* * * * *